United States Patent
Bailie et al.

(10) Patent No.: US 9,593,079 B2
(45) Date of Patent: Mar. 14, 2017

(54) STABILIZED MULTI-FUNCTIONAL ANTIOXIDANT COMPOUNDS AND METHODS OF USE

(71) Applicant: XPD HOLDINGS LLC, Ann Arbor, MI (US)

(72) Inventors: Marc Bailie, Manchester, MI (US); Steven K. Duddy, Ann Arbor, MI (US); Jim Herman, Grass Lake, MI (US)

(73) Assignee: XPD Holdings, LLC, Ann Arbor, MI (US)

( * ) Notice: Subject to any disclaimer, the term of this patent is extended or adjusted under 35 U.S.C. 154(b) by 0 days.

(21) Appl. No.: 15/066,487

(22) Filed: Mar. 10, 2016

(65) Prior Publication Data

US 2016/0185718 A1  Jun. 30, 2016

Related U.S. Application Data

(62) Division of application No. 14/408,145, filed as application No. PCT/US2013/049709 on Jul. 9, 2013, now Pat. No. 9,382,211.

(60) Provisional application No. 61/669,753, filed on Jul. 10, 2012.

(51) Int. Cl.
  *C07C 327/34*  (2006.01)
  *C07C 327/32*  (2006.01)
  *C07D 233/64*  (2006.01)

(52) U.S. Cl.
  CPC .......... *C07D 233/64* (2013.01); *C07C 327/34* (2013.01)

(58) Field of Classification Search
  CPC .......................... C07C 327/34; C07C 327/32
  USPC ........................................ 558/254, 255, 256
  See application file for complete search history.

(56) References Cited

U.S. PATENT DOCUMENTS

| | | | |
|---|---|---|---|
| 4,866,121 A | 9/1989 | Audhya et al. | |
| 6,060,512 A | 5/2000 | Yu et al. | |
| 6,610,664 B2 | 8/2003 | Lin et al. | |
| 2002/0128213 A1 | 9/2002 | Katz et al. | |

FOREIGN PATENT DOCUMENTS

WO   WO 2011098999   8/2011

OTHER PUBLICATIONS

Ashley, G., M. Burlingame, R. Desai, H. Fu, T. Leaf, P. Licari, C. Tran, D. Abbanat, K. Bush, and M. Macielag. "Preparation of Erythromycin Analogs having Functional Groups at C-15" Journ. Antibio. (2006), 59(7), pp. 392-401.*
International Search Report for PCT/US2013/049709, dated Mar. 27, 2014.

\* cited by examiner

*Primary Examiner* — Alicia L Otton
*Assistant Examiner* — Sagar Patel
(74) *Attorney, Agent, or Firm* — Honigman Miller Schwartz and Cohn LLP; Cynthia M. Bott; Jonathan P. O'Brien

(57) ABSTRACT

Disclosed are novel stable compounds having anti-oxidant properties and methods of using the compounds for the treatment of diseases or injuries associated with oxidative stress.

9 Claims, 6 Drawing Sheets

STABILIZED MULTI-FUNCTIONAL ANTIOXIDANT COMPOUNDS AND METHODS OF USE

CROSS-REFERENCE TO RELATED APPLICATION

This application is a divisional of U.S. patent application Ser. No. 14/408,145, filed Dec. 15, 2014, which is a United States National Phase of PCT/US2013/049709, filed Jul. 9, 2013, which claims the benefit of priority to U.S. Provisional Application Ser. No. 61/669,753, filed Jul. 10, 2012. The entire contents of which are incorporated herein by reference.

BACKGROUND

Many diseases, conditions and injuries are associated with reductions in the levels of antioxidant molecules and activity of antioxidant enzyme systems in affected tissues or organs and subsequent loss of cellular integrity secondary to oxidative stress. Oxidative stress represents an imbalance between production of reactive oxygen species and other oxidative molecules derived there from, for example lipid or other peroxides, and manifestation of reactive oxygen species and a biological system's ability to readily detoxify the reactive oxidant molecules or to repair the resulting damage. Reactive oxygen species can be beneficial, as they are used by the immune system as a way to attack and kill pathogens. In addition, some reactive oxidative species can act as intracellular or extracellular signaling molecules to trigger cellular responses through a process termed redox signaling. However, disturbances in the normal balance between oxidative and reductive processes in cells and tissues can cause toxic effects through excessive production of peroxides and free radicals that damage components of the cell, including proteins, carbohydrates, lipids, and DNA. Reduced antioxidant status may be a direct or indirect effect of a disease or insult. A deficiency of cellular antioxidants may lead to excess free radicals and other reactive oxygen species (ROS) the destructive effects of which can ultimately lead to cell death. The effects of oxidative stress depend upon the magnitude of the disturbance, with a cell being able to overcome small perturbations and regain its original state using natural antioxidant defenses, such as glutathione (GSH). GSH is synthesized by most cells and is one of the primary antioxidants responsible for maintaining the proper antioxidant status within the body.

However, under certain conditions, the normal physiologic supplies of GSH or other antioxidants are insufficient, the distribution is inadequate, or oxidative demands are too high to prevent cellular oxidation. Depressed antioxidant levels, either locally in particular cells or organs or systemically, have been associated with a number of clinically defined diseases and disease states which are the result of or which progress because of excessive free radical reactions and insufficient antioxidants.

Administration of reduced thiol containing compounds that provide either a substrate for generation of endogenous antioxidants such as glutathione, e.g. N-acetylcysteine, or are themselves directly or indirectly capable of scavenging reactive oxygen species, has been used to reestablish antioxidant status to ameliorate conditions of oxidative stress. However, chemical instability of thiol containing compounds limits shelf life under normal storage conditions, and particularly under extreme storage conditions and/or in common vehicles used for systemic administration. This property of chemical instability of thiol-containing antioxidants has limited widespread use of such compounds for treatment of disorders and diseases in which oxidative stress is a significant component of pathophysiology. Additionally, many thiol-containing antioxidant molecules and non-thiol antioxidant molecules have poor pharmaceutical properties, for example, low oral bioavailability or rapid clearance, which limits their utility.

Thus, there is a need for antioxidant compounds having improved pharmaceutical properties that are safe, potent, and stable even under extreme storage conditions, to normalize cellular antioxidant status in order to abrogate many of the untoward manifestations of the disease/injury associated with depletion of cellular oxidative defenses.

SUMMARY

It has now been found that compounds of this invention, and pharmaceutically acceptable compositions thereof, are potent and stable antioxidants useful for treatment of diseases or injuries associated with oxidative stress. The compounds of the present invention have the general Formula I or Formula II:

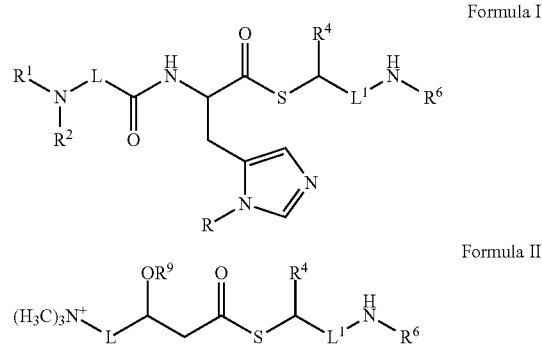

or a pharmaceutically acceptable salt thereof wherein R, $R^1$, $R^2$, $R^3$, L, $L^1$, $L^2$, $R^4$, $R^5$, $R^6$, $R^7$, $R^8$, $R^9$, m, n, and p, are described generally and in classes and subclasses below.

These compounds and pharmaceutically acceptable compositions are useful for preventing, treating or lessening the severity of a variety of diseases, injuries, or conditions, associated with reduced antioxidant levels and/or increased oxygen radical generation including, but not limited to, cardiovascular disease, e.g., atherosclerosis, myocardial infarction, chronic heart failure; chronic obstructive pulmonary disease; idiopathic pulmonary fibrosis; cerebral palsy; liver disease e.g., cirrhosis, and hepatitis; cystic fibrosis; dementia, e.g., dementia associated with Alzheimer's disease; inflammatory disease, e.g., inflammatory bowel disease, Crohn's disease, rheumatoid arthritis, and colitis; amyotrophic lateral sclerosis (ALS); acute respiratory distress syndrome (ARDS); infectious disease; lupus; eye disorders such as cataracts and macular degeneration; multiple sclerosis; kidney disease, e.g., nephropathy; neuropathy; encephalopathy; diabetes; beta thalessemia; sickle cell disease; Parkinson's disease; pulmonary fibrosis; reproductive diseases; infertility; seizure disorders; sepsis; stroke; gangrene; toxic shock; traumatic insult, e.g., exposure to bioweapons such as ricin, *Bacillus anthracis*, ebola virus, *Clostridium botulinum*, nipah virus, chemical or heat burns; contrast-induced nephropathy; drug overdose such as with acetaminophen or morphine; radiation exposure; exposure to cigarette smoke; exposure to toxic gas such a chlorine, mustard gas and sarin; blast injury; contact sensitivity reactions; delayed hypersensitivity reactions; hearing loss; envenomation; transplant rejection; gunshot; compression injury; toxicodendrin species associated inflammation; skin damage such as sunburn and wrinkles; spontaneous hemolysis or hemolysis induced by chemical or other agents, such as hemolytic anemia induced by anti-malarial treatments in susceptible individuals with glucose-6-phosphate dehydrogenase (G6PDH) deficiency; and chemotherapy treatment.

DETAILED DESCRIPTION

1. Definitions

Figure 1:
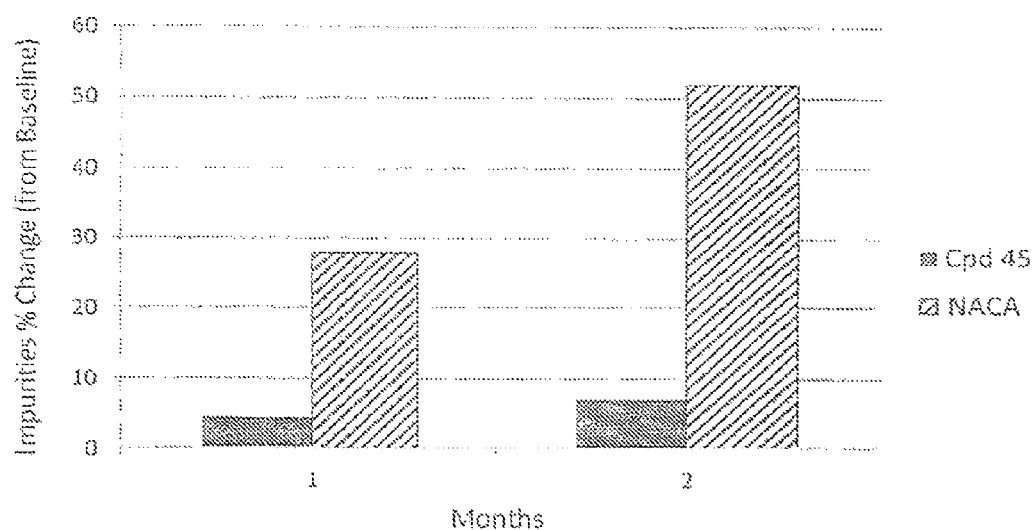
FIG. 1. Shows stability data for Compound 45 and NACA, as measured by content of impurities, after storage for one or two months at 5° C.

As used herein the following definitions shall apply unless otherwise indicated.

"SC" means subcutaneous injection.
"HOBT" means 1-hydroxybenzotriazole.
"IV" means intravenous injection or infusion.
"IM" means intramuscular injection.
"PG" means protecting group.
"ICM" means dimethylformamide.
"DCC" means dicyciohexylcarbodiimide.
"EDC" means ethylene dichloride.
"RH" means relative humidity.
"THF" means tetrahydrofuran.
"TMS" means trimethylsilane.
"Et" means ethyl.
"Me" means methyl.
"Pr" means propyl.
"Bu" means butyl.
"t-Bu" means tert-butyl.
"Boc" means tert-butoxycarbonyl.
"Pg" means protecting group.
"NACA" means N-acetylcysteine amide.

The compounds of the invention are contemplated for human and veterinary use. The term "subject", as used herein, includes without limitations humans, domestic animals and livestock such as cats, dogs, cattle, pigs, fowl, fish, and horses.

The term "treating" or other forms of the word such as "treatment", or "treat" is used herein to mean that administration of a compound of the present invention mitigates a disease or a disorder in a host and/or reduces, inhibits, or eliminates a particular characteristic or event associated with a disorder. Thus, the term "treatment" includes, preventing a disorder from occurring in a host, particularly when the host is predisposed to acquiring the disorder, inhibiting the disorder, and/or alleviating or reversing the disorder. Insofar as the methods of the present invention are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present invention may occur prior to onset of a disease. The term does not imply that the disease state be completely avoided.

As used herein, the term "pharmaceutically acceptable salt" of a compound refers to a salt which, within the scope of sound medical judgment, is suitable for use in contact with the tissues of humans and lower animals without undue toxicity, irritation, allergic response and the like, and are commensurate with a reasonable benefit/risk ratio.

As used herein, a "therapeutically effective amount" or "effective amount" means an amount necessary to delay the onset of, inhibit the progress of, relieve the symptoms of, or reverse a condition being treated.

Throughout the description and claims of this specification the word "comprise" and other forms of the word, such as "comprising" and "comprises," means including but not limited to, and is not intended to exclude, for example, other additives, components, integers, or steps.

As used herein, the singular forms "a", "an", and "the" include plural references unless the context clearly dictates otherwise.

The terms "alkyl" and "alkyl group" are used interchangeably and mean a linear, branched, saturated or unsaturated carbon chain having 1 to 20 carbon atoms. The number of carbon atoms can be expressed, for example, "$C_{1-6}$ alkyl" which means that the alkyl group has one to six carbon atoms. Examples of such groups include methyl, ethyl, n-propyl, isopropyl, n-butyl, isobutyl, sec-butyl, tert-butyl, pentyl, 1,4-dienyl, but-1-enyl and the like.

A "substituted alkyl group" means an alkyl group which is substituted with one or more group independently selected from OH, alkyl, cycloalkyl, halogen, phenyl, benzyl, amide, amine, aldehyde, ester, or ether.

The terms "cycloalkyl" and "cycloalkyl group" are used interchangeably and mean a saturated mono-ring carbocycle with three to seven atoms on the ring. Examples of such groups include cyclopropyl, cyclobutyl, cyclopentyl, cyclohexyl, and cycloheptyl.

A "substituted cycloalkyl group" means a cycloalkyl group which is substituted with one or more group independently selected from OH, alkyl, cycloalkyl, halogen, phenyl, benzyl, amide, amine, aldehyde, ester, or ether.

The term "alkoxy" refers to an alkyl, alkenyl, alkynyl, or cycloalkyl group attached via an oxygen atom, for example —O-alkyl, and the like. Alkoxy groups can be optionally substituted as described above for substituted alkyl.

Any reference in the claims to "optionally substituted" includes "unsubstituted" and "substituted". Where a group is designated as "unsubstituted" then that group is not substituted.

Unless otherwise stated, structures depicted or described herein are also meant to include all isomeric (e.g., enantiomeric, diastereomeric, geometric, or conformational) forms of the structures, e.g., the R and S configurations for each asymmetric center. Accordingly, single stereochemical isomers as well as enantiomeric, diastereomeric, geometric, or conformational mixtures of the present compounds are within the scope of the invention.

Unless otherwise stated, the compounds of this invention include their pharmaceutically acceptable salts, prodrugs, or derivatives.

2. Compounds of the Invention

The compounds of the present invention are stable during storage but convert rapidly in the body into two distinct antioxidant molecules. The properties of stability and biological availability are clue to a chemical linkage that stabilizes the thiol component of the molecules and improves the pharmaceutical properties of the component antioxidant species. One of these antioxidant molecules is a thiol-containing antioxidant. Free thiol-containing molecules are reactive and generally unstable during storage and oxidize to form disulfides devoid of antioxidant properties. In some embodiments, the compound is a compound of formula I which is converted into a thiol-containing antioxidant such as N-acetylcysteine and N-acetylcysteine amide, and a beta-alanyl-histidine derivative such as, carnosine and derivatives of carnosine such as N-acetylcarnosine. The thiol-containing antioxidant is capable of reacting with oxidized glutathione to generate reduced glutathione. Beta-alanyl-histidine derivatives have a number of antioxidant properties. For example, carnosine has been shown to scavenge reactive oxygen species (ROS) as well as alpha-beta unsaturated aldehydes formed from peroxidation of cell membrane fatty acids during oxidative stress. In other embodiments, the compound is a compound of formula II which is converted into a thiol-containing antioxidant such as N-acetylcysteine or N-acetylcysteine amid; and L-carnitine or a derivative of carnitine such as acetyl-L-carnitine and propionyl-L-carnitine. Carnitines exert a substantial antioxidant action, thereby providing a protective effect against lipid peroxidation of phospholipid membranes and against oxidative stress induced at the myocardial and endothelial cell level. Carnitine serves as a substrate in the regeneration of Coenzyme A (CoA).

The present invention provides compounds of Formula I or Formula II:

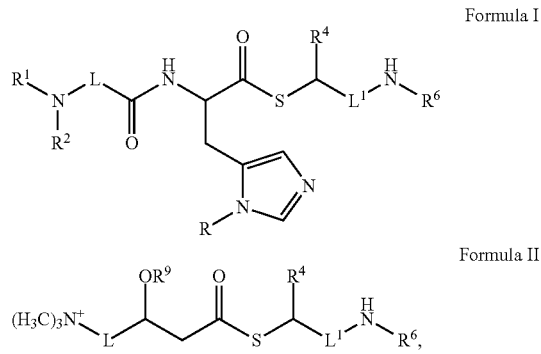

or a pharmaceutically acceptable salt thereof wherein:

R is H or optionally substituted alkyl or an optionally substituted alkoxy;

$R^1$ and $R^2$ are each independently H, optionally substituted alkyl, or —C(=O)$R^3$;

$R^3$ is optionally substituted alkyl or optionally substituted alkoxy;

L is —$(CH_2)_m$—;

$L^1$ is —CH($R^5$)— or —C(=O)—;

$L^2$ is —O— or —NH—;

$R^4$ is H or optionally substituted alkyl;

$R^5$ is H, —C(O)OH, or —C(=O)$L^2R^7$;

$R^6$ is H or —$(CH_2)_n$(=O)$R^8$;

$R^7$ is H, alkyl, or —$(CH_2)_p$C(=O)OH $R^8$ is —OH, —$CH_3$, —$CH_2$C(=O)OH, or —(—$CH_2)_w$—CH($NH_2$)—C(=O)OH;

$R^9$ is H, alkyl, or —C(=O)alkyl;

m is 1, 2, 3, or 4; and n, p, and w, are each independently 0, 1, 2, 3, or 4.

In another embodiment the invention provides compounds of Formula I or Formula II, or a pharmaceutically acceptable salt thereof wherein:

R is H or $C_{1-6}$ alkyl or $C_{1-6}$ alkoxy;

$R^1$ and $R^2$ are each independently H, $C_{1-6}$ alkyl, or —C(=O)$R^3$;

$R^3$ is $C_{1-6}$ alkyl or $C_{1-6}$ alkoxy;

L is —$(CH_2)_m$—;

$L^1$ is —CH($R^5$)— or —C(=O)—;

$L^2$ is —O— or —NH—;

$R^4$ is H or $C_{1-6}$ alkyl;

$R^5$ is H, —C(O)OH, or —C(=O)$L^2R^7$;

$R^6$ is H, —$(CH_2)_n$C(=O)$R^8$;

$R^7$ is H, $C_{1-6}$ alkyl, or —$(CH_2)_p$C(=O)OH $R^8$ is —OH, —$CH_3$, —$CH_2$C(=O)OH, or —$(CH_2)_w$—CH($NH_2$)—C(=O)OH;

$R^9$ is H, $C_{1-6}$ alkyl, or —C(=O)$C_{1-6}$ alkyl;

m is 1, 2, 3, or 4; and n, p, and w, are each independently 0, 1, 2, 3, or 4.

In some embodiments R is H, optionally substituted alkyl, or optionally substituted alkoxy. In another embodiment, R is unsubstituted alkyl. In another embodiment, R is optionally substituted $C_{1-6}$ alkyl. In another embodiment, R is unsubstituted $C_{1-6}$ alkyl. In another embodiment, R is optionally substituted $C_{1-6}$ alkoxy. In another embodiment, R is unsubstituted $C_{1-6}$ alkoxy.

In some embodiments $R^1$ is H and $R^2$ is H. In another embodiment, $R^1$ is H and $R^2$ is optionally substituted alkyl. In another embodiment, $R^1$ is H and $R^2$ is unsubstituted alkyl. In another embodiment, $R^1$ is H and $R^2$ is optionally substituted $C_{1-6}$ alkyl. In another embodiment, $R^1$ is H and $R^2$ is unsubstituted $C_{1-6}$ alkyl. In another embodiment, $R^1$ is H and $R^2$ is —C(=O)$R^3$, and $R^3$ is optionally substituted alkyl. In another embodiment, $R^1$ is H and $R^2$ is —C(=O)$R^3$, and $R^3$ is unsubstituted alkyl. In another embodiment, $R^1$ is H and $R^2$ is —C(=O)$R^3$, and $R^3$ is optionally substituted $C_{1-6}$ alkyl. In another embodiment, $R^1$ is H and $R^2$ is —C(=O)$R^3$, and $R^3$ is unsubstituted $C_{1-6}$ alkyl.

In some embodiments $R^1$ is H and $R^2$ is —C(=O)$R^3$, and $R^3$ is optionally substituted alkoxy. In another embodiment, $R^1$ is H and $R^2$ is —C(=O)$R^3$, and $R^3$ is unsubstituted alkoxy. In another embodiment, $R^1$ is H and $R^2$ is —C(=O)$R^3$, and $R^3$ is optionally substituted $C_{1-6}$ alkoxy. In another embodiment, $R^1$ is H and $R^2$ is —C(=O)$R^3$, and $R^3$ is unsubstituted $C_{1-6}$ alkoxy.

In other embodiments L is —$(CH_2)_m$— and m is 1. In another embodiment, L is —$(CH_2)_m$— and m is 2. In another embodiment, L is —$(CH_2)_m$— and m is 3. In another embodiment, L is —$(CH_2)_m$— and m is 4.

In some embodiments $L^2$ is —O—. In another embodiment, $L^2$ is —NH—.

In still other embodiments $R^4$ is H. In another embodiment, $R^4$ is or optionally substituted alkyl. In another embodiment, $R^4$ is unsubstituted alkyl. In another embodiment, $R^4$ is optionally substituted $C_{1-6}$ alkyl. In another embodiment, $R^4$ is unsubstituted $C_{1-6}$ alkyl.

In yet other embodiments $R^5$ is H. In another embodiment, $R^5$ is —C(O)OH. In another embodiment, $R^5$ is —C(=O)$L^2R^7$.

In some embodiments $R^6$ is H. In another embodiment, $R^6$ is —(CH$_2$)$_n$C(=O)$R^8$.

In some embodiments $R^7$ is H. In another embodiment, $R^7$ is optionally substituted alkyl. In another embodiment, $R^7$ is unsubstituted alkyl. In another embodiment, $R^7$ is optionally substituted $C_{1-6}$ alkyl. In another embodiment, $R^7$ is unsubstituted $C_{1-6}$ alkyl. In another embodiment, $R^7$ is (CH)$_p$C(=O)OH.

In other embodiments $R^8$ is —OH. In another embodiment, $R^8$ is —CH$_3$, In another embodiment, $R^8$ is —CH$_2$C(=O)OH. In another embodiment, $R^8$ is —(CH$_2$)$_w$—CH(NH$_2$)—C(=O)OH.

In some embodiments $R^9$ is H. In another embodiment, $R^9$ is alkyl, In another embodiment, $R^9$ is $C_{1-6}$ alkyl. In another embodiment, $R^9$ is —C(=O)alkyl. In another embodiment, $R^9$ is —C(=O)$C_{1-6}$ alkyl, In another embodiment, $R^9$ is —CH$_3$. In another embodiment, $R^9$ is —CH$_2$CH$_3$. In another embodiment, $R^9$ is —(CH$_2$)$_2$CH$_3$. In another embodiment, $R^9$ is —(CH$_2$)$_3$CH$_3$. In another embodiment, $R^9$ is —(CH$_2$)$_4$CH$_3$. In another embodiment, $R^9$ is —(CH$_2$)$_5$CH$_3$. In another embodiment, $R^9$ is —C(=O)CH$_3$. In another embodiment, $R^9$ is —C(=O)CH$_2$CH$_3$. In another embodiment, $R^9$ is —C(=O)(CH$_2$)$_2$CH$_3$. In another embodiment, $R^9$ is —C(=O)(CH$_2$)$_3$CH$_3$. In another embodiment, $R^9$ is —C(=O)(CH$_2$)$_4$CH$_3$. In another embodiment, $R^9$ is —C(=O)(CH$_2$)$_5$CH$_3$.

In still other embodiments n is 0. In another embodiment, n is 1. In another embodiment, n is 2. In another embodiment, n is 3. In another embodiment, n is 4.

In some embodiments p is 0. In another embodiment, p is 1. In another embodiment, p is 2. In another embodiment, p is 3. In another embodiment, p is 4.

In some embodiments w is 0. In another embodiment, w is 1. In another embodiment, w is 2. In another embodiment, w is 3. In another embodiment, w is 4.

In one aspect, the invention provides compounds of Formula I,

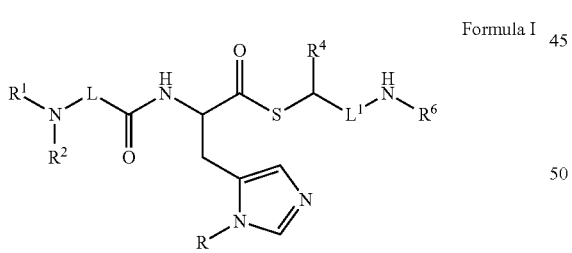

Formula I wherein R, $R^1$, $R^2$, $R^4$, $R^5$, $R^6$, L, and $L^1$ are defined as above In some embodiments, R is H, methyl, propyl, or tert-butoxycarbonyl. In a further embodiment, R is H. In another further embodiment, R is methyl. In still another further embodiment, R is propyl. In another further embodiment, R is tert-butoxycarbonyl.

In some embodiments, $R^1$ is H.

In some embodiments, $R^2$ is H, —C(O)Me, or tert-butoxycarbonyl. In a further embodiment, $R^2$ is H. In another further embodiment, $R^2$ is —C(O)Me. In another further embodiment, $R^2$ is tert-butoxycarbonyl.

In one embodiment, R and $R^2$ are each tert-butoxycarbonyl.

In some embodiments, $R^4$ is H or methyl. In a further embodiment, $R^4$ is H. In another further embodiment, $R^4$ is methyl.

In one embodiment, is —CHR$^5$—, wherein $R^5$ is H, —C(O)NH$_2$, —C(O)OH, —C(O)OCH$_3$, or

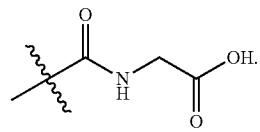 [SMILES: *C(=O)NCC(=O)O]

In one further embodiment, $R^5$ is H. In another further embodiment $R^5$ is —C(O)NH$_2$. In another further embodiment $R^5$ is —C(O)OH. In another further embodiment $R^5$ is —C(O)OCH$_3$. In another further embodiment $R^5$ is

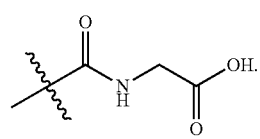 [SMILES: *C(=O)NCC(=O)O]

In still another embodiment, $L^1$ is —C(=O)—.

In some embodiments, $R^6$ is H, —C(O)Me, —(CH$_2$)COOH, or

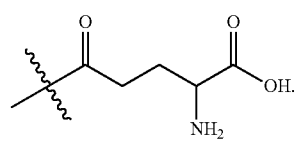 [SMILES: *C(=O)CCC(N)C(=O)O]

In one further embodiment, $R^6$ is H. In another further embodiment $R^6$ is —C(O)Me. In another further embodiment $R^6$ is —(CH$_2$)COOH. In another further embodiment $R^6$ is

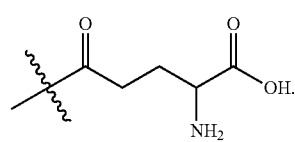

In one embodiment, L is —(CH$_2$)$_m$—, wherein m is 2 or 3. In a further embodiment, m is 2. In another further embodiment, m is 3.

In another aspect, the invention provides compounds of Formula Ia,

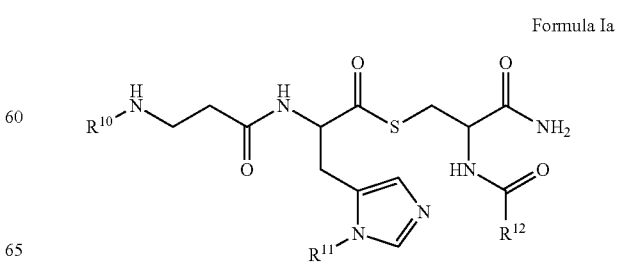

Formula Ia wherein $R^{10}$ and $R^{11}$ are each independently H, optionally substituted alkyl, or —C(O)$R^3$, wherein $R^3$ is defined above; and $R^{12}$ is —OH, —CH$_3$, —CH$_2$C(=O)OH, or —(CH$_2$)$_w$—CH(NH$_2$)—C(=O)OH, wherein w is defined above.

In one embodiment, $R^{10}$ and $R^{11}$ are each independently H, C$_{1-4}$ alkyl, —(C=O)—C$_{1-4}$ alkyl, or —(C=O)—OC$_{1-4}$ alkyl.

In another embodiment, $R^{12}$ is —CH$_3$, —CH$_2$C(=O)OH, or —(CH$_2$)$_2$—CH(NH$_2$)—C(=O)OH.

In one embodiment, $R^{10}$ and $R^{11}$ are each independently H, C$_{1-4}$ alkyl, or —C(O)Me.

In another embodiment, $R^{12}$ is —CH$_3$.

In another embodiment, $R^{10}$ and $R^{11}$ are each independently tert-butoxycarbonyl.

In another aspect, the invention provides compounds of Formula Ib,

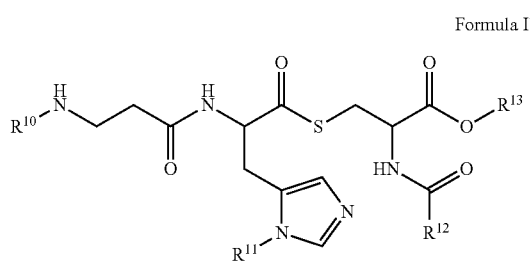

Formula Ib wherein $R^{10}$ and $R^{11}$ are each independently H, optionally substituted alkyl, or —C(=O)$R^3$, wherein $R^3$ is defined above;

$R^{12}$ is —OH, —CH$_3$, —CH$_2$C(=O)OH, or —(CH$_2$)$_w$—CH(NH$_2$)—C(=O)OH, wherein w is defined above; and $R^{13}$ is H, alkyl, or —(CH$_2$)$_p$C(=O)OH.

In one embodiment, $R^{10}$ and $R^{11}$ are each independently H, C$_{1-4}$ alkyl, —(C=O)—C$_{1-4}$ alkyl, or —(C=O)—OC$_{1-4}$ alkyl.

In another embodiment, $R^{12}$ is —CH$_3$, —CH$_2$C(=O)OH, or —(CH$_2$)$_2$—CH(NH$_2$)—C(=O)OH.

In one embodiment, $R^{13}$ is H or alkyl. In a further embodiment, $R^{13}$ is H.

In one embodiment, $R^{10}$ and $R^{11}$ are each independently H, C$_{1-4}$ alkyl, or —C(O)Me.

In another embodiment, $R^{12}$ is —CH$_3$.

In a another embodiment $R^{13}$ is C$_{1-6}$ alkyl. In a further embodiment, $R^{13}$ is methyl, ethyl, propyl, isopropyl, butyl, isobutyl, tert-butyl, or pentyl. In still a further embodiment, $R^{13}$ is methyl.

In another embodiment, $R^{19}$ and $R^{11}$ are each independently tert-butoxycarbonyl.

In one aspect, the invention provides compounds of Formula II,

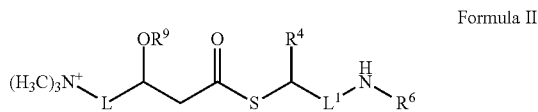

Formula II wherein L, L$^1$, R$^9$, R$^4$, and R$^6$ are defined above.

In one embodiment, L is CH$_2$.
In one embodiment, R$^4$ is H.
In one embodiment, R$^6$ is —C(O)Me.
In one embodiment R$^9$ is H, —C(O)Me, or —C(O)Et. In a further embodiment, R$^9$ is H. In another further embodiment, R$^9$ is —C(O)Me. In a further embodiment, R$^9$ is —C(O)Et.

In one embodiment, L$^1$ is —CHR$^5$, and R$^5$ is —COOH or —C(O)NH$_2$. In one further embodiment, R$^5$ is —COOH. In another further embodiment, R$^5$ is —C(O)NH$_2$.

Specific compounds of the invention include those described in Table 1.

TABLE I

| Cpd. No. | Structure | Name |
|---|---|---|
| 1 | ![structure 1] | (2S)-S-2,3-diamino-3-oxopropyl 2-(3-aminopropanamido)-3-(1H-imidazol-5-yl) propanethioate |
| 2 | ![structure 2] | 2-amino-3-((S)-2-(3-aminopropanamido)-3-(1H-imidazol-5-yl)propanoylthio)propanoic acid |

TABLE I-continued

| Cpd. No. | Structure | Name |
|---|---|---|
| 3 | 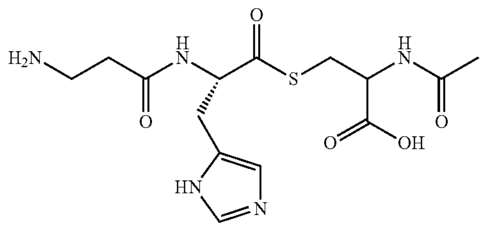 [SMILES: CC(=O)NC(CSC(=O)[C@H](Cc1cnc[nH]1)NC(=O)CCN)C(=O)O] | 2-acetamido-3((S)-2-(3-aminopropan-amido)-3-(1H-imidazol-5-yl)propanoylthio)propanoic acid |
| 4 | 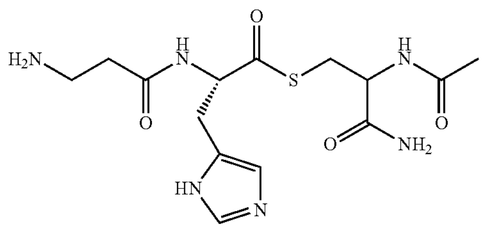 [SMILES: CC(=O)NC(CSC(=O)[C@H](Cc1cnc[nH]1)NC(=O)CCN)C(N)=O] | (2S)-S-2-acetamido-3-amino-3-oxopropyl 2-(3-aminopropanamido)-3-(1H-imidazol-5-yl) propanethioate |
| 5 | 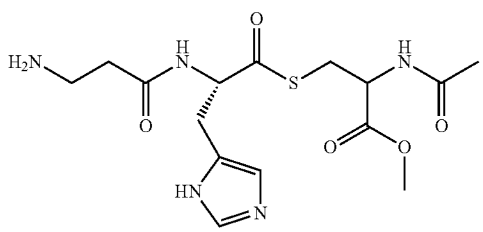 [SMILES: COC(=O)C(CSC(=O)[C@H](Cc1cnc[nH]1)NC(=O)CCN)NC(C)=O] | methyl 2-acetamido-3-((S)-2-(3-aminopropanamido)-3-(1H-imidazol-5-yl) propanoylthio)propanoate |
| 6 | 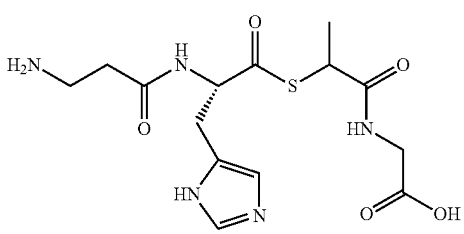 [SMILES: CC(SC(=O)[C@H](Cc1cnc[nH]1)NC(=O)CCN)C(=O)NCC(=O)O] | 2-(2-((S)-2-(3-aminopropanamido)-3-(1H-imidazol-5-yl)propanoylthio)-propanamido)acetic acid |
| 7 | 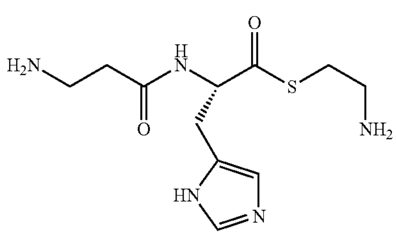 [SMILES: NCCSC(=O)[C@H](Cc1cnc[nH]1)NC(=O)CCN] | (S)-S-2-aminoethyl-2-(3-aminopropanamido)-3-(1H-imidazol-5-yl)propanethioate |
| 8 | 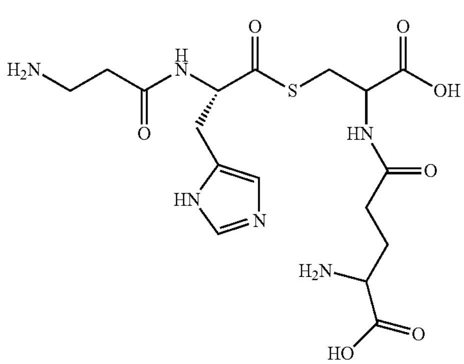 [SMILES: NCCC(=O)N[C@@H](Cc1cnc[nH]1)C(=O)SCC(NC(=O)CCC(N)C(=O)O)C(=O)O] | 2-amino-5-(2-((S)-2-(3-aminopropan-amido)-3-(1H-imidazol-5-yl)propanoylthio)-1-carboxyethylamino)-5-oxopentanoic acid |

TABLE I-continued

| Cpd. No. | Structure | Name |
|---|---|---|
| 9 | 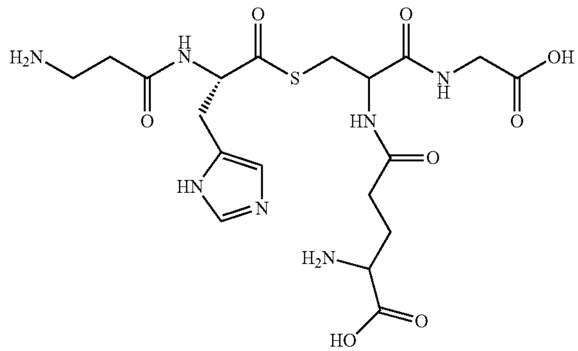 [SMILES: NCCC(=O)N[C@@H](Cc1cnc[nH]1)C(=O)SCC(NC(=O)CCC(N)C(=O)O)C(=O)NCC(=O)O] | 2-amino-5-(3-((S)-2-(3-aminopropan-amido)-3-(1H-imidazol-5-yl)propanoylthio)-1-(carboxymethylamino)-1-oxopropan-2-ylamino)-5-oxopentanoic acid |
| 10 | 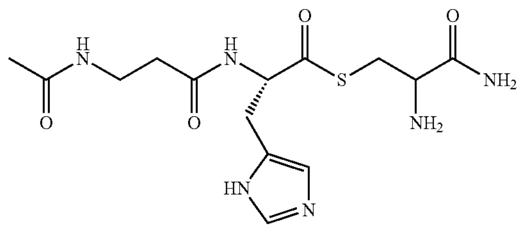 [SMILES: CC(=O)NCCC(=O)N[C@@H](Cc1cnc[nH]1)C(=O)SCC(N)C(N)=O] | (2S)-S-2,3-diamino-3-oxopropyl 2-(3-acetamidopropanamido)-3-(1H-imidazol-5-yl)propanethioate |
| 11 | 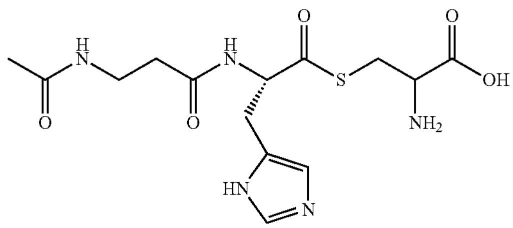 [SMILES: CC(=O)NCCC(=O)N[C@@H](Cc1cnc[nH]1)C(=O)SCC(N)C(=O)O] | 3-((S)-2-(3-acetamidopropanamido)-3-(1H-imidazol-5-yl)propanoylthio)-2-aminopropanoic acid |
| 12 | 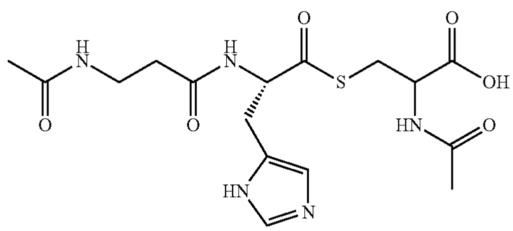 [SMILES: CC(=O)NCCC(=O)N[C@@H](Cc1cnc[nH]1)C(=O)SCC(NC(C)=O)C(=O)O] | (8S)-8-((1H-imidazol-5-yl)methyl)-2,7,10,14-tetraoxo-6-thia-3,9,13-triazapentadecane-4-carboxylic acid |
| 13 | 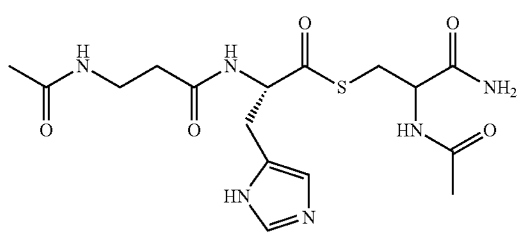 [SMILES: CC(=O)NCCC(=O)N[C@@H](Cc1cnc[nH]1)C(=O)SCC(NC(C)=O)C(N)=O] | (2S)-S-2-acetamido-3-amino-3-oxopropyl-2-(3-acetamidopropanamido)-3-(1H-imidazol-5-yl)propanethioate |
| 14 | 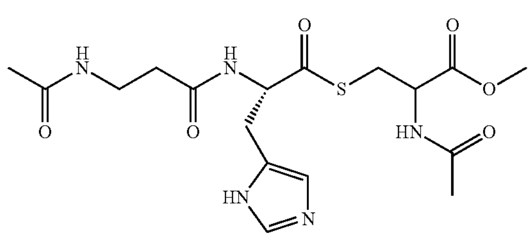 [SMILES: COC(=O)C(CSC(=O)[C@H](Cc1cnc[nH]1)NC(=O)CCNC(C)=O)NC(C)=O] | (8S)-methyl-8-((1H-imidazol-5-yl)methyl)-2,7,10,14-tetraoxo-6-thia-3,9,13-triaza-pentadecane-4-carboxylate |

TABLE I-continued

| Cpd. No. | Structure | Name |
| --- | --- | --- |
| 15 | 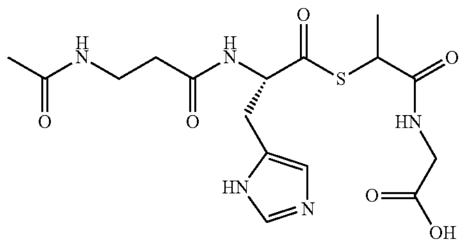 [SMILES: CC(=O)NCCC(=O)N[C@@H](Cc1cnc[nH]1)C(=O)SC(C)C(=O)NCC(=O)O] | 2-(2-{[(2S)-2-(3-acetamidopropanamido)-3-(1H-imidazol-5-yl)propanoyl]sulfanyl}propanamido) acetic acid |
| 16 | 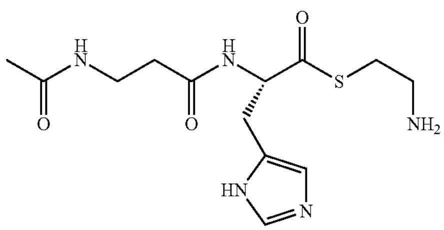 [SMILES: CC(=O)NCCC(=O)N[C@@H](Cc1cnc[nH]1)C(=O)SCCN] | (S)-S-2-aminoethyl-2-(3-acetamidopropanamido)-3-(1H-imidazol-5-yl)propanethioate |
| 17 | 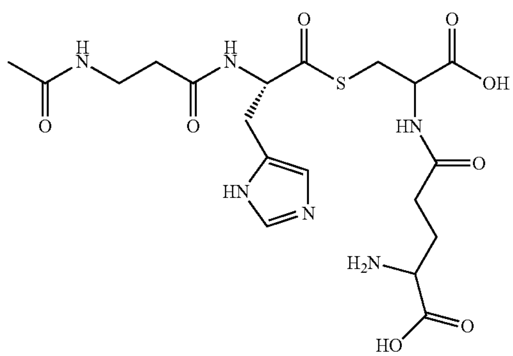 [SMILES: CC(=O)NCCC(=O)N[C@@H](Cc1cnc[nH]1)C(=O)SCC(NC(=O)CCC(N)C(=O)O)C(=O)O] | 2-amino-4-[(1-carboxy-2-{[(2S)-2-(3-acetamidopropanamido)-3-(1H-imidazol-5-yl)propanoyl]sulfanyl}ethyl)carbamoyl] botanic acid |
| 18 | 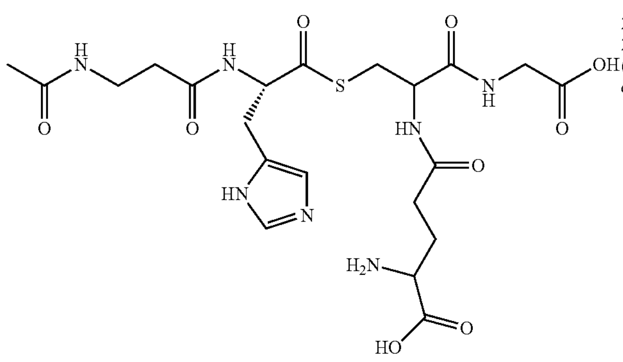 [SMILES: CC(=O)NCCC(=O)N[C@@H](Cc1cnc[nH]1)C(=O)SCC(NC(=O)CCC(N)C(=O)O)C(=O)NCC(=O)O] | 2-amino-4-({1-[(carboxymethyl)carbamoyl]-2-{[(2S)-2-(3-acetamidopropanamido)-3-(1H-imidazol-5-yl)propanoyl]sulfanyl}-ethyl} carbamoyl)butanoic acid |
| 19 | 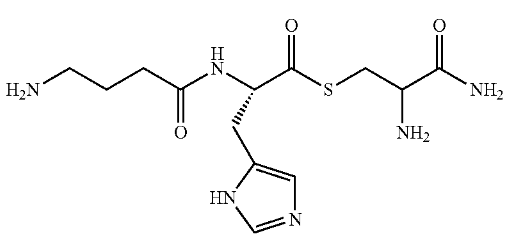 [SMILES: NCCCC(=O)N[C@@H](Cc1cnc[nH]1)C(=O)SCC(N)C(N)=O] | (2S)-S-2,3-diamino-3-ozopropyl 2-(4-aminobutanamido)-3-(1H-imidazol-5-yl) propanethioate |

TABLE I-continued

| Cpd. No. | Structure | Name |
|---|---|---|
| 20 | 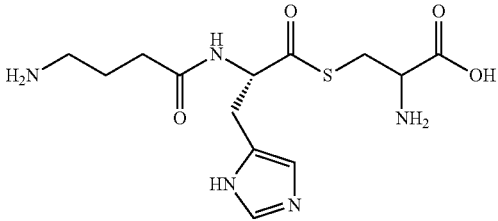 [SMILES: NCCCC(=O)N[C@@H](Cc1cnc[nH]1)C(=O)SCC(N)C(=O)O] | 2-amino-3-((S)-2-(4-aminobutanamido)-3-(1H-imidazol-5-yl)propanoylthio)-propanoic acid |
| 21 | 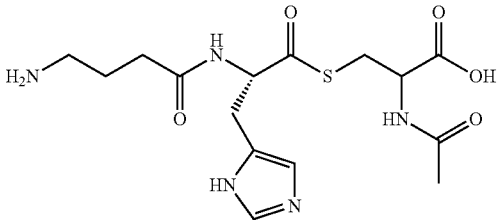 [SMILES: CC(=O)NC(CSC(=O)[C@H](Cc1cnc[nH]1)NC(=O)CCCN)C(=O)O] | 2-acetamido-3-((S)-2-(4-aminobutanamido)-3-(1H-imidazol-5-yl)propanoylthio)propanoic acid |
| 22 | 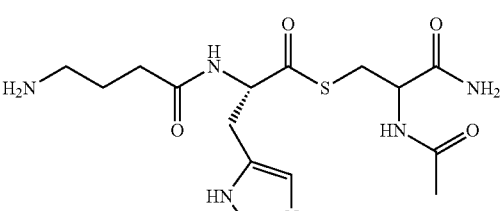 | (2S)-S-2-acetamido-3-amino-3-oxopropyl-2-(4-aminobutanamido)-3-(1H-imidazol-5-yl) propanethioate |
| 23 | 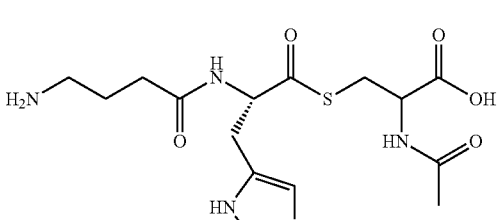 | methyl 2-acetamido-3-((S)-2-(4-aminobutanamido)-3-(1H-imidazol-5-yl)propanoylthio)-propanoate |
| 24 | 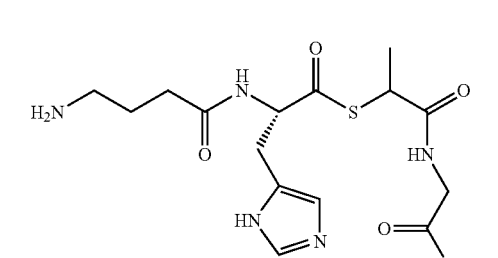 | 2-(2-((S)-2-(4-aminobutanamido)-3-(1H-imidazol-5-yl)propanoylthio)propan-amido) acetic acid |
| 25 | 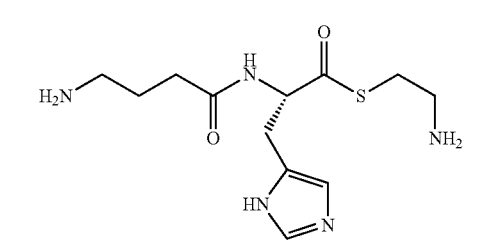 [SMILES: NCCCC(=O)N[C@@H](Cc1cnc[nH]1)C(=O)SCCN] | (S)-S-2-aminoethyl-2-(4-aminobutanamido)-3-(1H-imidazol-5-yl) propanethioate |

TABLE I-continued

| Cpd. No. | Structure | Name |
|---|---|---|
| 26 | 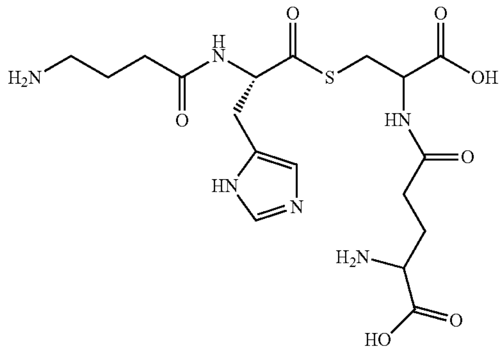 [SMILES: NCCCC(=O)N[C@@H](Cc1cnc[nH]1)C(=O)SCC(NC(=O)CCC(N)C(=O)O)C(=O)O] | 2-amino-5-(2-((S)-2-(4-aminobutan-amido)-3-(1H-imidazol-5-yl)propanoylthio)-1-carboxyethylamino)-5-oxopentanoic acid |
| 27 | 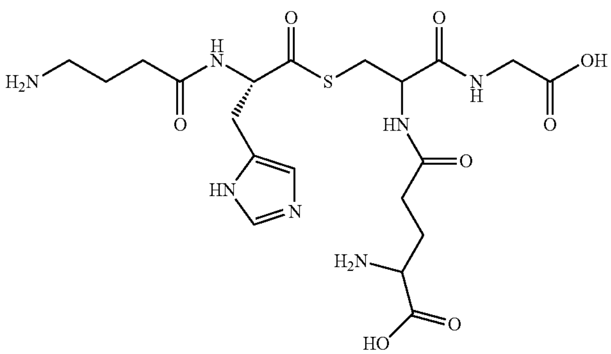 [SMILES: NCCCC(=O)N[C@@H](Cc1cnc[nH]1)C(=O)SCC(NC(=O)CCC(N)C(=O)O)C(=O)NCC(=O)O] | 2-amino-5-(3-((S)-2-(4-aminobutan-amido)-3-(1H-imidazol-5-yl)propartoylthio)-1-(carboxymethylamino)-1-oxopropan-2-ylamino)-5-oxopentanoic acid |
| 28 | 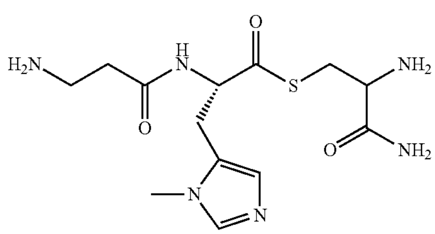 [SMILES: Cn1cncc1C[C@H](NC(=O)CCN)C(=O)SCC(N)C(N)=O] | (2S)-S-2,3-diamino-3-oxopropyl-2-(3-aminopropanamido)-3-(1-methyl-1H-imidazol-5-yl)propanethioate |
| 29 | 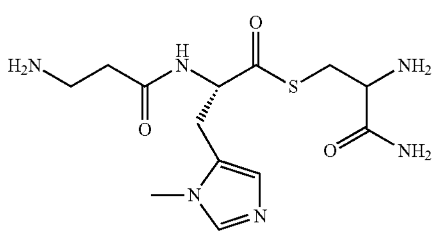 [SMILES: Cn1cncc1C[C@H](NC(=O)CCN)C(=O)SCC(N)C(N)=O] | 2-amino-3-((S)-2-(3-aminopropan-amido)-3-(1-methyl-1H-imidazol-5-yl)propanoylthio)propanoic acid |
| 30 | 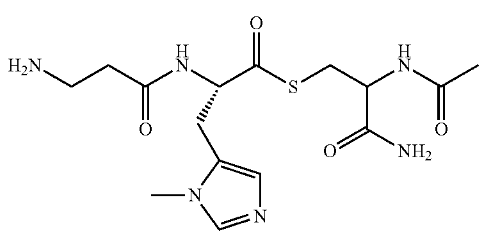 [SMILES: CC(=O)NC(CSC(=O)[C@H](Cc1cncn1C)NC(=O)CCN)C(N)=O] | 2-acetamido-3-((S)-2-(3-aminopropan-amido)-3-(1-methyl-1H-imidazol-5-yl)propanoylthio)propanoic acid |

TABLE I-continued

| Cpd. No. | Structure | Name |
|---|---|---|
| 31 | 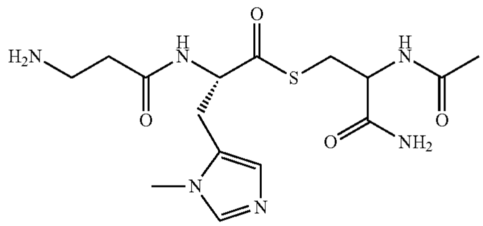 [SMILES: CC(=O)NC(CSC(=O)[C@H](Cc1cncn1C)NC(=O)CCN)C(N)=O] | (2S)-S-2-acetamido-3-amino-3-oxopropyl 2-(3-aminopropanamido)-3-(1-methyl-1H-imidazol-5-yl)propanethioate |
| 32 | 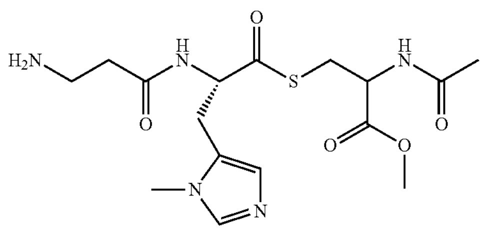 [SMILES: COC(=O)C(CSC(=O)[C@H](Cc1cncn1C)NC(=O)CCN)NC(C)=O] | methyl 2-acetamido-3-((S)-2-(3-aminopropan-amido)-3-(1-methyl-1H-imidazol-5-yl)propanoyl-thio)propanoate |
| 33 | 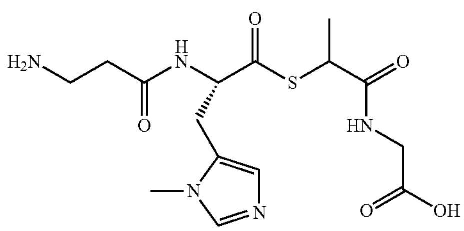 [SMILES: CC(SC(=O)[C@H](Cc1cncn1C)NC(=O)CCN)C(=O)NCC(=O)O] | 2-(2-((S)-2-(3-aminopropanamido)-3-(1-methyl-1H-imidazol-5-yl)propanoyl-thio)propanamido) acetic acid |
| 34 | 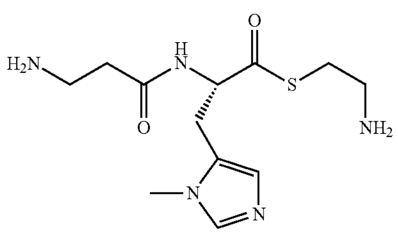 [SMILES: Cn1cncc1C[C@H](NC(=O)CCN)C(=O)SCCN] | (S)-S-2-aminoethyl-2-(3-aminopropanamido)-3-(1-methyl-1N-imidazol-5-yl)propanethioate |
| 35 | 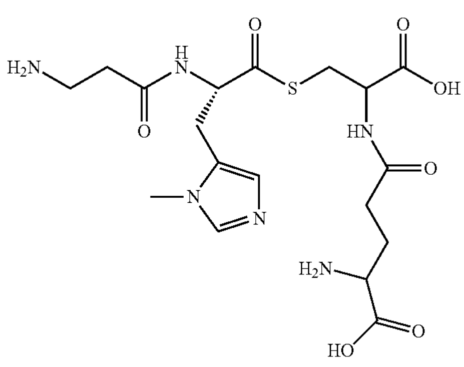 [SMILES: Cn1cncc1C[C@H](NC(=O)CCN)C(=O)SCC(NC(=O)CCC(N)C(=O)O)C(=O)O] | 2-amino-5-(2-((S)-2-(3-aminopropan-amido)-3-(1-methyl-1H-imidazol-5-yl)propanoyl-thio)-1-carboxyethylamino)-5-oxopentanoic acid |

TABLE I-continued

| Cpd. No. | Structure | Name |
|---|---|---|
| 36 | 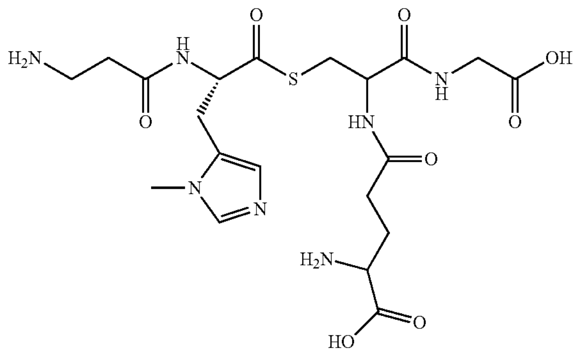 [SMILES: Cn1cncc1C[C@H](NC(=O)CCN)C(=O)SCC(NC(=O)CCC(N)C(=O)O)C(=O)NCC(=O)O] | 2-amino-5-(3-((S)-2-(3-aminopropan-amido)-3-(1-methyl-1H-imidazol-5-yl)propan-oylthio)-1-(carboxymethylamino)-1-oxopropan-2-ylamino)-5-oxopentanoic acid |
| 37 | 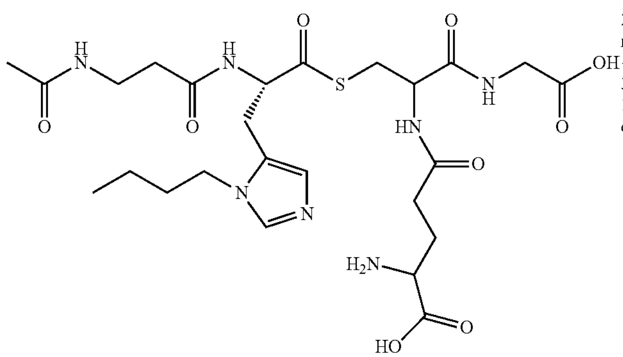 [SMILES: CCCCn1cncc1C[C@H](NC(=O)CCNC(C)=O)C(=O)SCC(NC(=O)CCC(N)C(=O)O)C(=O)NCC(=O)O] | 2-amino-4-({1-[(carboxymethyl)caraba-moyl]-2-{[(2S)-2-(3-acetamidopropanamido)-3-(1-butyl-1H-imidazol-5-yl)propanoyl]sulfanyl}-ethyl} carbamoyl)butanoic acid |
| 38 | 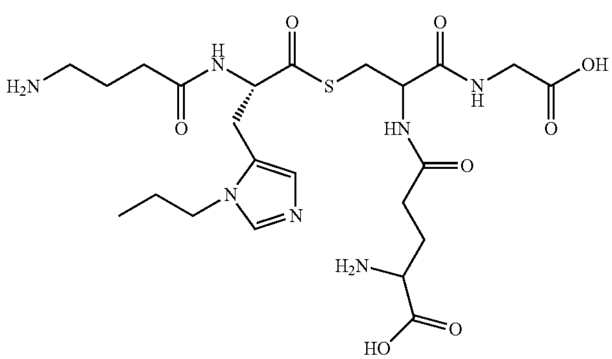 [SMILES: CCCn1cncc1C[C@H](NC(=O)CCCN)C(=O)SCC(NC(=O)CCC(N)C(=O)O)C(=O)NCC(=O)O] | 2-amino-5-(3-((S)-2-(4-aminobutan-amido)-3-(1-propyl-1H-imidazol-5-yl)propanoyl-thio)-1-(carboxymethylamino)-1-oxopropan-2-ylamino)-5-oxopentanoic acid |
| 39 | 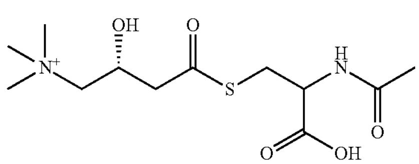 [SMILES: CC(=O)NC(CSC(=O)C[C@@H](O)C[N+](C)(C)C)C(=O)O] | (2R)-4-(2-acetamido-2-carboxyethylthio)-2-hydroxy-N,N,N-trimethyl-4-oxobutan-1-aminium |
| 40 | 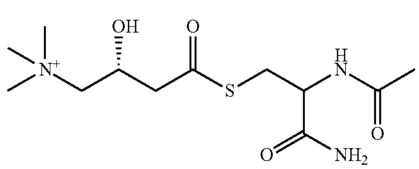 [SMILES: CC(=O)NC(CSC(=O)C[C@@H](O)C[N+](C)(C)C)C(N)=O] | (2R)-4-(2-acetamido-3-amino-3-oxopropylthio)-2-hydroxy-N,N,N-trimethyl-4-oxobutan-1-aminium |

TABLE I-continued

| Cpd. No. | Structure | Name |
|---|---|---|
| 41 | 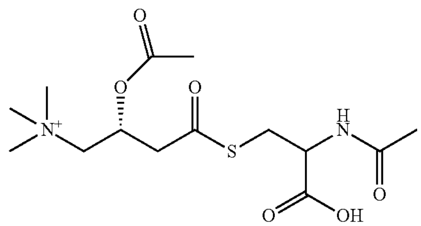 [SMILES: CC(=O)NC(CSC(=O)C[C@H](C[N+](C)(C)C)OC(C)=O)C(=O)O] | (2R)-4-(2-acetamido-2-carboxyethylthio)-2-acetoxy-N,N,N-trimethyl-4-oxobutan-1-aminium |
| 42 | 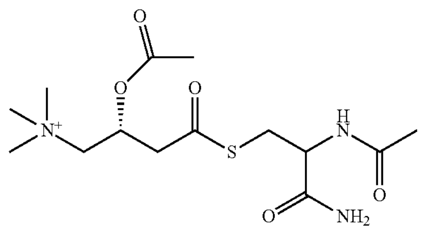 | (2R)-4-(2-acetamido-3-amino-3-oxopropyithio)-2-acetoxy-N,N,N-trimethyl-4-oxobutan-1-aminium |
| 43 | 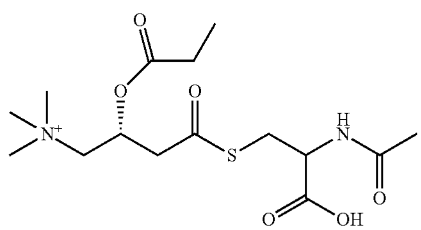 [SMILES: CCC(=O)O[C@H](CC(=O)SCC(NC(C)=O)C(=O)O)C[N+](C)(C)C] | (2R)-4-(2-acetamido-2-carboxyethylthio)-N,N,N-trimethyl-4-oxo-2-(propionyloxy)butan-1-aminium |
| 44 | 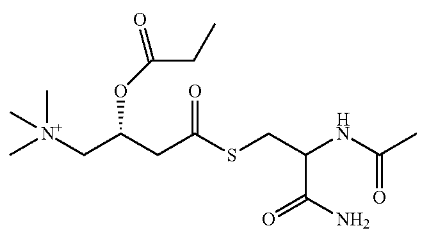 [SMILES: CCC(=O)O[C@H](CC(=O)SCC(NC(C)=O)C(N)=O)C[N+](C)(C)C] | (2R)-4-(2-acetamido-3-amino-3-oxopropylthio)-N,N,N-trimethyl-4-oxo-2-(propionyloxy)butan-1-aminium |
| 45 | 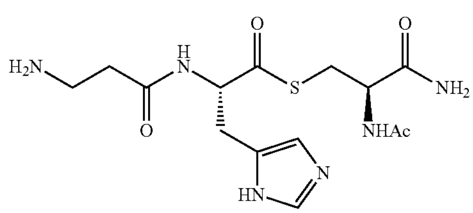 [SMILES: CC(=O)N[C@@H](CSC(=O)[C@H](Cc1cnc[nH]1)NC(=O)CCN)C(N)=O] | (S)-S-((R)-2-acetamido-3-amino-3-oxopropyl) 2-(3-aminopropanamido)-3-(1H-imidazol-5-yl)propanethioate |
| 46 | 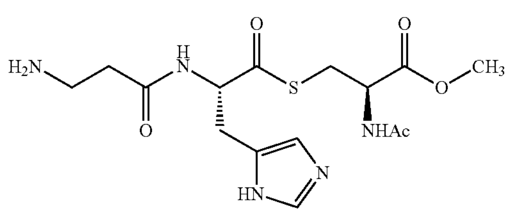 [SMILES: COC(=O)[C@H](CSC(=O)[C@H](Cc1cnc[nH]1)NC(=O)CCN)NC(C)=O] | (R)-methyl 2-acetamido-3-(((S)-2-(3-aminopropanamido)-3-(1H-imidazol-5-yl)propanoyl)thio)propanoate |

The present invention also provides pharmaceutical compositions each containing one or more of the compounds described or specifically named above and a pharmaceutically acceptable carrier, adjuvant, or vehicle.

In certain embodiments, the compounds of the present invention can be used in combination therapy with other drugs. Such therapies include, but are not limited to simultaneous or sequential administration of the drugs involved. For example, compounds of the present invention can be administered with drugs that are commonly used as a standard of care for a particular condition. Thus, in certain embodiments, these compositions optionally further comprise one or more additional therapeutic agents.

Pharmaceutically acceptable salts are well known in the art. For example, S. M. Berge et al. describe pharmaceutically acceptable salts in detail in J. Pharm. Sci., 1977, 66:1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared, e.g., by first reacting the purified compound in its free-based form with a suitable organic or inorganic acid and then isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil-soluble or dispersible products may be obtained by such quaternization.

Base addition salts can be prepared, e.g., by first reacting the purified compound in its acid form with a suitable organic or inorganic base and then isolating the salt thus formed. Base addition salts include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, lower alkyl sulfonate, or aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

3. Methods of the Invention

The compounds of the invention are administered alone, or in combination with other suitable agents, to reduce, prevent or counteract oxidative stress, free radical oxidant formation and overproduction in cells and tissues, and the damage to cellular components such as proteins, lipids, nucleic acids and other cellular biomolecules, as well act to help regenerate reduced glutathione. The present invention additionally provides for methods of treating a disease, injury, or condition, associated with reduced antioxidant levels and/or increased oxygen radical generation.

In some embodiments the method of treating a disease, injury, or condition, associated with reduced antioxidant levels and/or increased oxygen radical generation comprises administering to a subject in need thereof, a therapeutically effective amount of a compound of the invention.

One embodiment of the invention is a method of treating cardiovascular disease, cerebral palsy; liver disease, cystic fibrosis, dementia, inflammatory disease, amyotrophic lateral sclerosis, acute respiratory distress syndrome, infectious disease, lupus, eye disorders, multiple sclerosis, kidney disease, neuropathy, encephalopathy, diabetes; beta thalessemia, sickle cell disease, Parkinson's disease, pulmonary fibrosis, reproductive diseases, infertility; seizure disorders, sepsis, stroke, gangrene, toxic shock, or traumatic insult, comprising administering to a subject in need thereof, a therapeutically effective amount of a compound of the invention.

Another embodiment is a method of treating atherosclerosis, myocardial infarction, chronic obstructive pulmonary disease, or chronic heart failure comprising administering to a subject in need thereof, a therapeutically effective amount of a compound of the invention.

Still another embodiment is a method of treating spontaneous hemolysis. Another embodiment is a method of treating hemolysis induced by chemical or other agents. In certain embodiments the method is a method of treating hemolytic anemia induced by anti-malarial treatments, in susceptible individuals with glucose-6-phosphate dehydrogenase (G6PDH) deficiency; and chemotherapy treatment.

Yet another embodiment is a method of treating inflammatory bowel disease, Crohn's disease, rheumatoid arthritis, or colitis comprising administering to a subject in need thereof, a therapeutically effective amount of a compound of the invention.

Another embodiment is a method of treating cirrhosis, or hepatitis comprising administering to a subject in need thereof, a therapeutically effective amount of a compound of the invention.

Still another embodiment is a method of treating dementia associated with Alzheimer's disease.

Yet another embodiment is a method of treating cataracts or macular degeneration.

Another embodiment is a method of treating traumatic insult. In some embodiments the traumatic insult is exposure to bioweapons. In some embodiments the bioweapon is ricin. Or the bioweapon is *Bacillus anthracis*. Or the bioweapon is ebola virus. Or the bioweapon is *Clostridium botulinum*. Or the bioweapon is nipah virus.

Or the traumatic insult is a chemical burn. Or the traumatic insult is a heat burn. Or the traumatic insult is contrast-induced nephropathy. Or the traumatic insult is radiation exposure. Or the traumatic insult is exposure to cigarette smoke. Or the traumatic insult is exposure to toxic gas. Or the traumatic insult is blast injury. Or the traumatic insult is a contact sensitivity reaction. Or the traumatic insult is a delayed hypersensitivity reaction. Or the traumatic insult is an insult that results in hearing loss. Or the traumatic insult is envenomation. In some embodiments the envenomation is caused by a snake bite. Or the envenomation is caused by a spider sting. Or the envenomation is caused by a jelly fish. Or the envenomation is caused by a scorpion sting. Or the envenomation is caused by a insect sting. Or the traumatic insult is sunburn. Or the traumatic insult is transplant rejection. Or the traumatic insult is a gunshot. Or the traumatic insult is a compression injury. Or the traumatic insult is toxicodendrin species associated inflammation. Or the traumatic insult is skin damage. Or the traumatic insult is chemotherapy treatment. Or the traumatic insult is drug overdose. In some embodiments the drug overdose is an overdose of acetaminophen. Or the drug overdose is an overdose of morphine.

4. Formulations and Administration

Compounds of the present invention can be formulated as pharmaceutical compositions and administered to a mammalian subject, such as a human subject in a variety of forms adapted to the chosen route of administration, i.e., orally, topically, including vaginal and rectal administration, via inhalation, and parenterally, by intravenous, intramuscular or subcutaneous routes.

As described herein, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Pharmaceutical compositions suitable for the delivery of compounds of the present disclosure and methods for their preparation will be readily apparent to those skilled in the art. Such compositions and methods for their preparation may be found, for example, in Remington's Pharmaceutical Sciences, 19th Edition (Mack Publishing Company, 1995).

Suitable dosage forms for oral administration include, for example, solid, semi-solid and liquid systems such as in hard or soft shell gelatin capsules, tablets, liquids, powders, lozenges (including liquid-filled), chews, gels, films, ovules, sprays, elixirs, suspensions, syrups, buccal/mucoadhesive patches and the like.

Oral dosage forms may, for example, contain the following: binders such as gum tragacanth, acacia, corn starch or gelatin; excipients such as dicalcium phosphate; a disintegrating agent such as corn starch, potato starch, alginic acid, and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices. The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

For topical administration, the present compounds may be applied in pure form, i.e., when they are liquids. However, it will generally be desirable to administer them to the skin as compositions or formulations, in combination with a dermatological acceptable carrier, which may be a solid or liquid. Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of the present disclosure to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The compounds of the invention are preferably formulated in dosage unit form for ease of administration and uniformity of dosage. The expression "dosage unit form" as used herein refers to a physically discrete unit of agent appropriate for the subject to be treated. Useful dosages of the compounds of the present disclosure can be determined by comparing their in vitro activity, and in vivo activity in animal models. Methods for the extrapolation of effective dosages in mice, and other animals, to humans are known to the art; for example, see U.S. Pat. No. 4,938,949. It will be understood, however, that the total daily usage of the compounds and compositions of the present invention will be decided by the attending physician within the scope of sound medical judgment. The specific effective dose of compound required for treatment will vary from subject to subject, depending on the species, age, body weight and general condition of the subject, the disorder being treating, the severity of the infection, mode of administration, the duration of the treatment; drugs used in combination or coincidental with the specific compound employed, and like factors well known in the medical arts.

EXAMPLES

General Syntheses:

Compounds of the present invention can be readily prepared by methods known in the art. Illustrated below are exemplary methods for the preparation of compounds of the present invention. The methods described below are for illustration purposes, and should not be regarded as limiting the invention.

Scheme 1 illustrates the coupling of an intermediate acid of Formula A and a thiol of Formula B to produce the compounds of Formula I.

Scheme 1: Coupling of Intermediate acid A and thiol B

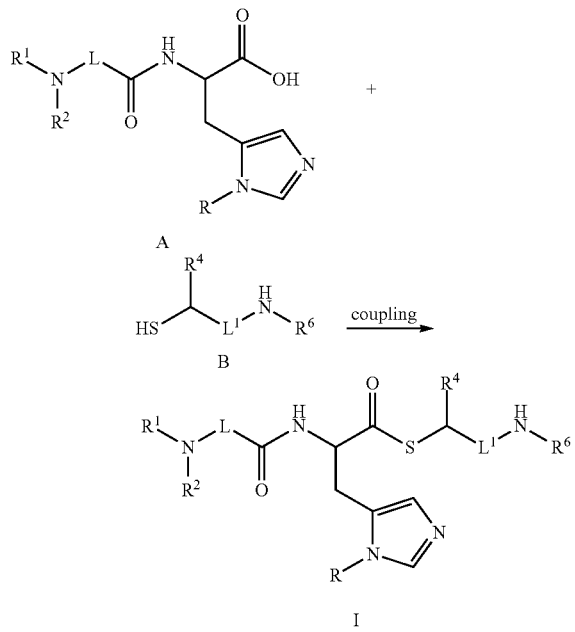

In Scheme I above, intermediate acid A can be coupled with thiol B to produce compounds of Formula I using standard coupling conditions know in the art. Non-limiting examples of coupling reagents are DCC/HOBt, EDC/HOBt, and TP3®. The coupling reaction can be performed in the presence of a solvent and, optionally, a base. Solvents and bases suitable for the above described coupling reactions are known to those having skill in the art.

Intermediate acids of Formula A are either commercially available, or can be synthesized by methods known in the art. For example, intermediates of Formula A can be synthesized by the coupling of histidine derivatives of Formula A1 with various amino acids of Formula A2, followed by deprotection where appropriate, according to Scheme 1a below.

Scheme 1a: Synthesis of intermediates of Formula A

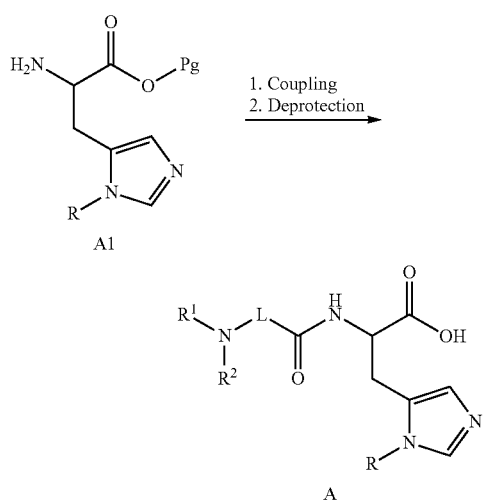

Thiol intermediates of Formula B are either commercially available, or can be synthesized by methods known in the art.

In the event that $R^1$, $R^2$ and/or R is hydrogen, the amine functionalities of intermediate acid A can first be protected with an appropriate amine protecting group. Such protecting groups are known in the art, and non-limiting examples are Boc, Fmoc, cbz, and acyl. Scheme 2 below illustrates the synthesis of compounds of Formula I using protecting groups.

Scheme 2: Protection of Intermediate acid A and followed by coupling with thiol B

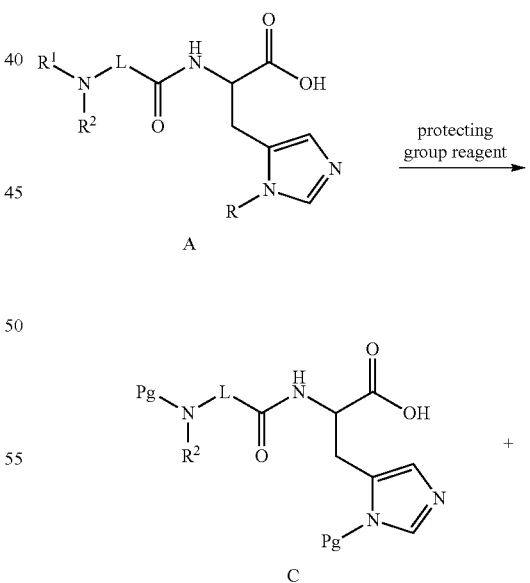

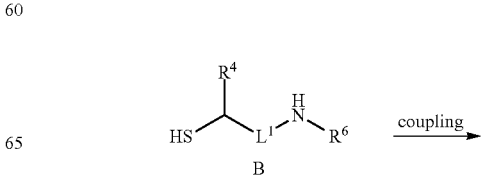

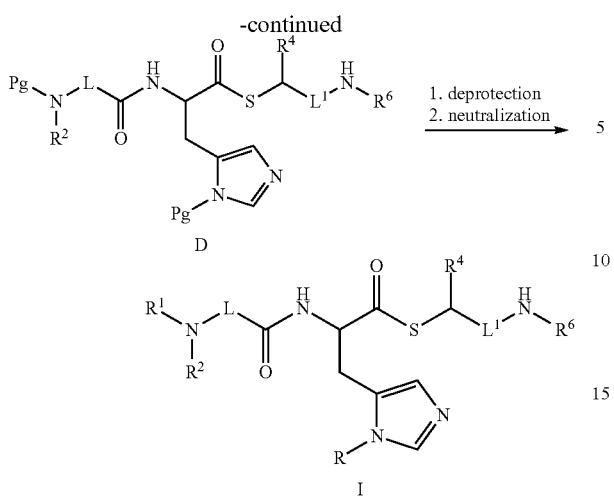

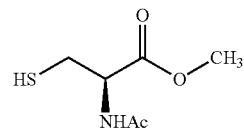

In Scheme 2, Intermediate A is first contacted with an amine protecting group reagent, such as di-tert-butyl dicarbonate. An exemplary synthesis is described in *New Journal of Chemistry* 24(12), 1037-1042, 2000. The protected form of A is then coupled with Intermediate B, and then deprotected under conditions appropriate for the protecting group, such as a strong acid neat or in an aprotic solvent, such as dioxane. Neutralization of the compound of Formula I can be accomplished using a moderate base, such as triethylamine in an organic solvent, such as ethyl acetate.

Scheme 3 illustrates the coupling of intermediate acid E and thiol B to produce the compounds of Formula II.

Scheme 3: Coupling of Intermediate acid E and thiol B

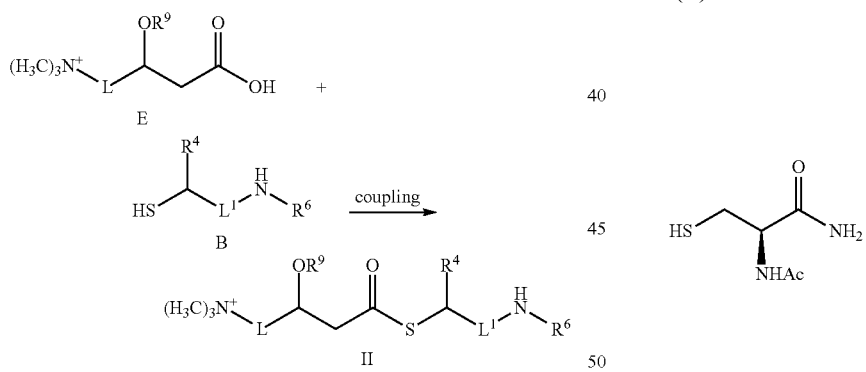

In Scheme 3 above, intermediate acid E can be coupled with thiol B to produce compounds of Formula II using standard coupling conditions know in the art. Non-limiting examples of coupling conditions are DCC/HOBt, EDC/HOBt, and TP3®. The coupling reaction can be performed in the presence of a solvent and, optionally, a base. Solvents and bases suitable for the above described coupling reactions are known to those having skill in the art. Intermediates of the Formula E are either commercially available, or can be readily synthesized using methods known in the art.

SPECIFIC EXAMPLES

The Examples described below are provided so the invention can be better understood, and should not be regarded as limiting the invention.

Preparative Example 1

(R)-methyl 2-acetamido-3-mercaptopropanoate (45a)

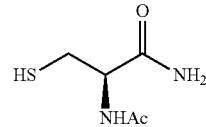

To a solution of (R)-2-acetamido-3-mercaptopropanoic acid, N-acetyl-(L)-cysteine (50 g, 0.30 mol) in 500 mL of methanol was added 0.5 mL of acetyl chloride. The solution was stirred at room temperature for 48 h at which time another 0.5 mL of acetyl chloride was added. The solution was stirred overnight then concentrated to a viscous liquid. Trituration with hexanes afforded the methyl ester as white solid. The product was dried under high vacuum at room temperature for 4 h to give 53.4 g (~100%) of (R)-methyl 2-acetamido-3-mercaptopropanoate. $^1$HNMR (CDCl$_3$) δ 6.39 (bs, 1H), 4.90 (m, 1H), 3.79 (s, 3H), 3.01 (d, 2H), 2.06 (s, 3H).

Preparative Example 2

(R)-2-Acetamido-3-mercaptopropanamide (45b)

45a (53.4 g, 0.30 mol) was diluted with 250 mL of toluene and 200 mL of ammonium hydroxide. The mixture was stirred at room temperature overnight then concentrated. The resulting residue was suspended in 250 mL of acetonitrile/H$_2$O (9.3:1) and stirred at room temperature until the insoluble material formed a viscous paste. The solvent was decanted then concentrated to give a viscous liquid. The crude product was taken up in dichloromethane/methanol (8.5:1) and passed through a silica gel column eluting with dichloromethane/methanol (8.5:1). Fractions containing the least polar UV-active component were combined and concentrated to give 25 g (52%) of (R)-2-acetamido-3-mercaptopropanamide as white solid. $^1$HNMR (DMSO-d$_6$) δ 8.0 (d, 1H), 7.41 (s, 1H), 7.13 (s, 1H), 4.33 (m, 1H), 2.76 (m, 1H), 2.65 (m, 1H), 2.22 (m, 1H), 1.88 (s, 3H).

Preparative Example 3

(S)-3-(1-(tert-butoxycarbonyl)-1H-imidazol-5-yl)-2-(3-((tert-butoxycarbonyl)amino)propanamido)propanoic acid (45c)

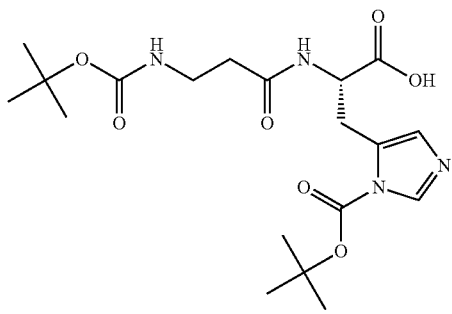 [SMILES: CC(C)(C)OC(=O)NCCC(=O)N[C@@H](Cc1cncn1C(=O)OC(C)(C)C)C(=O)O]

To a stirring biphasic mixture of (S)-2-(3-aminopropanamido)-3-(1H-imidazol-5-yl)propanoic acid, L-Carnosine (25.0 g, 110.5 mmol) in 200 mL of dioxane and 200 mL of water containing NaOH (4.86 g, 121.51 mmol) at ~0° C. under $N_2$, was added dropwise a solution of di-tert-butyl dicarbonate (53.1 g, 243.3 mmol) in 150 mL of dioxane. After allowing the solution to warm to room temperature overnight, the sample was acidified with the addition of 200 mL of saturated $KH_2PO_4$ solution, concentrated, then extracted with EtOAc (2×500 mL). The combined organic extracts were dried with $MgSO_4$, filtered and concentrated to give 35.74 g (76%) of 45c as white solid. MS (APCI) m/z 427 [M+H]$^+$.

Example 1

(S)—S—((R)-2-acetamido-3-amino-3-oxopropyl) 2-(3-aminopropanamido)-3-(1H-imidazol-5-yl)propanethioate dihydrochloride (45)

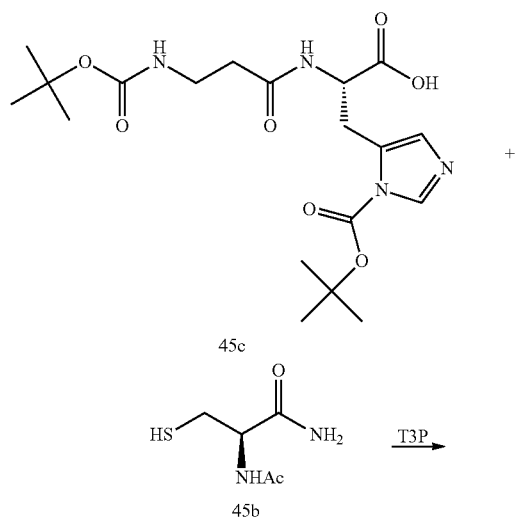

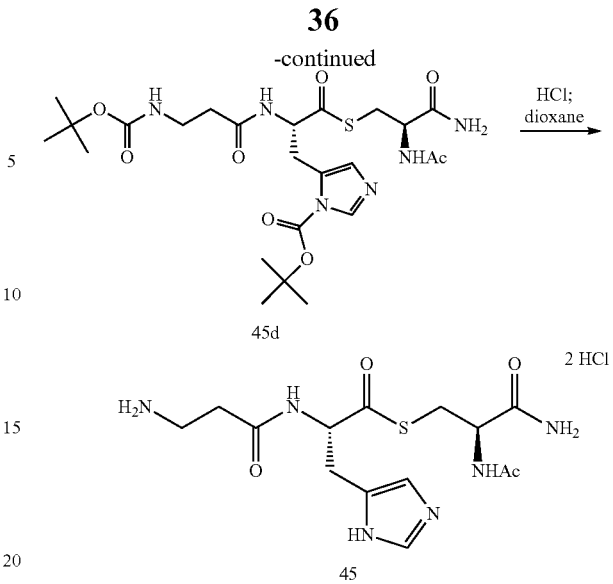

Step 1: To a stirring suspension at room temperature under $N_2$ of (S)-3-(1-(tert-butoxycarbonyl)-1H-imidazol-5-yl)-2-(3-(tert-butoxycarbonylamino)propanamido)propanoic acid (45c, 35.74 g, 83.80 mmol) and (R)-2-acetamido-3-mercaptopropanamide (45b, 13.59 g, 83.78 mmol) in 500 mL of THF:EtOAc (1:1) was added dropwise triethylamine (26 mL, 186 mmol). After addition, the suspension was stirred for 15 minutes then propylphosphonic anhydride, 50 wt. % solution in EtOAc (55 mL, 92 mmol) was added dropwise. The resultant cloudy solution was stirred at room temperature for 2 h then saturated $NaHCO_3$ solution (~500 mL) was added. The layers were separated and the organic extract was washed with saturated $KH_2PO_4$ and then saturated NaCl solution. The aqueous phases were back extracted (in the same order) with fresh EtOAc (2×500 mL). The combined organic extracts were dried using $MgSO_4$, filtered, concentrated and chromatographed twice (silica gel, 50% THF in EtOAc) to give 35.53 g (74%) of tert-butyl 5-((S)-3-((R)-2-acetamido-3-amino-3-oxopropylthio)-2-(3-(tert-butoxycarbonylamino)propanamido)-3-oxopropyl)-1H-imidazole-1-carboxylate (45d) as white foamy solid. MS (APCI) m/z 571 [M+H]$^+$.

Step 2: To a mechanically stirring solution at room temperature under $N_2$ of tert-butyl 5-((S)-3-((R)-2-acetamido-3-amino-3-oxopropylthio)-2-(3-(tert-butoxycarbonylamino)propanamido)-3-oxopropyl)-1H-imidazole-1-carboxylate (45 d, 104.1 g, 182.4 mmol) in 1200 mL of dioxane was added dropwise hydrogen chloride, 4 N solution in dioxane (106 mL, 640 mmol). After addition of 50 mL of the HCl solution, solid formed. After complete addition, the sample was stirred at room temperature under $N_2$ for 3 h, filtered and vacuum dried to give 97.9 g (>100%) of titled compound as white solid. MS (APCI) m/z 371 [parent+H]$^+$.

The product was then dissolved in 600 mL of water and was lyophilized to give 91.3 g of (S)—S—((R)-2-acetamido-3-amino-3-oxopropyl) 2-(3-aminopropanamido)-3-(1H-imidazol-5-yl)propanethioate dihydrochloride salt as white foamy solid. MS (APCI) m/z 371 [parent+H]$^+$. $^1$H NMR (400 MHz, $D_2O$) δ 8.46 (s, 1H), 7.14 (s, 1H), 4.72-4.77 (m, 1H), 4.60-4.68 (bs, water peak), 4.42-4.42 (m, 1H), 3.26-3.36 (m, 1H), 3.15-3.22 (m, 1H), 2.96-3.10 (m, 4H), 2.50-2.63 (m, 2H) and 1.82-1.90 (m, 3H). Analysis: Calcd for $C_{14}H_{22}N_6O_4S \times 2.3HCl \times 0.65H_2O$ (466.003): C, 36.08; H, 5.54; N, 18.03; Cl, 17.50. Found: C, 35.93; H, 5.42; N, 17.66; Cl, 17.22. HPLC 99.8% (240 nM), $R_t$ 6.54 min.

Example 2

(R)-methyl 2-acetamido-3-(((S)-2-(3-aminopropanamido)-3-(1H-imidazol-5-yl)propanoyl)thio)propanoate dihydrochloride (46)

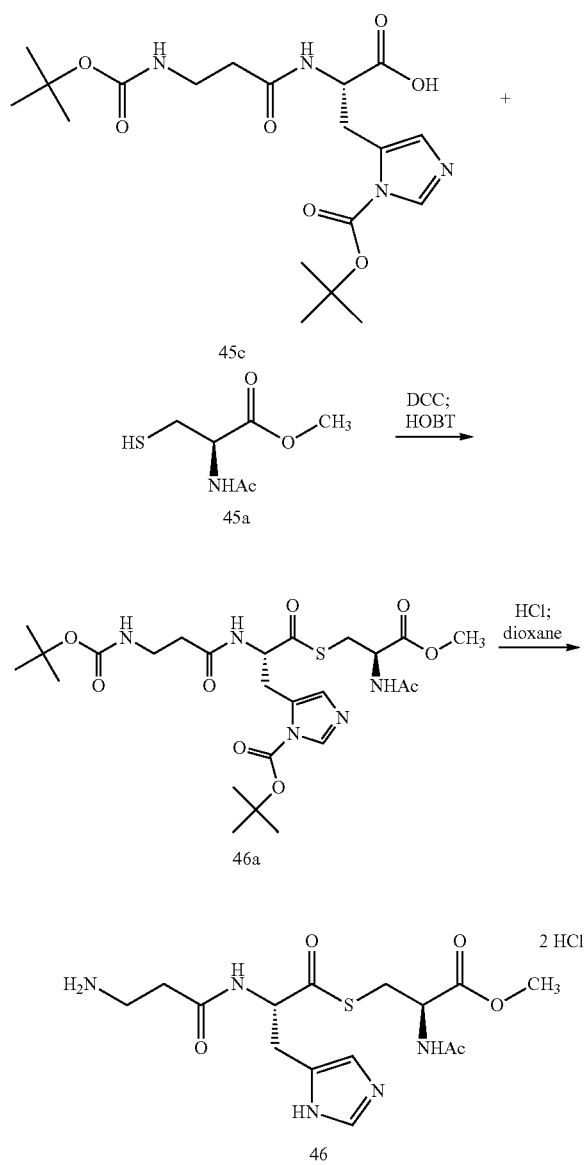

Step 1: A mixture of bis-BOC-L-carnosine (45c, 0.855 g, 2.0 mmol), 1-hydroxybenzotriazole hydrate (0.405 g, 2.6 mmol), N-acetylcysteine methyl ester (45a, 0.434 g, 2.45 mmol) and ethyl acetate (50 mL) was cooled in an ice bath and stirred 10 minutes under an atmosphere of nitrogen gas. Then dicyclohexylcarbodiimide (0.433 g, 2.1 mmol) was added and the mixture was stirred at zero degrees as the cooling bath was allowed to slowly warm to room temperature. After about one hour a precipitate had formed and the product was present by mass spectral analysis. The reaction mixture was stirred overnight at room temperature and was then filtered through a pad of celite. The filtered solution was then washed with saturated aqueous sodium bicarbonate solution (3×20 mL) and brine (20 mL), and the organic layer was dried over magnesium sulfate, filtered and concentrated to an oil. The oil was chromatographed on silica gel (230-400 mesh, 32.5 g) using ethyl acetate and then ethyl acetate/tetrahydrofuran, 4/1, v/v as the eluant. The product was obtained as a white foam, 0.475 g. MS: $(M+1)^+=586.2$ (30%); 486.2 (100%); 386.1 (96%).

Step 2: 5-[2-(2-Acetylamino-2-methoxycarbonyl-ethylsulfanylcarbonyl)-2-(3-tert-butoxycarbonylamino-propionylamino)-ethyl]-imidazole-1-carboxylic acid tert-butyl ester (46a, 0.1028 g, 0.175 mmol) in dry dioxane (2 mL) was added dropwise to 4N HCl in dioxane (5.0 mL, 114 mmol) and the mixture was stirred about 2 hours at room temperature. The reaction mixture was concentrated to dryness and residual volatiles removed in high vacuum. The product was obtained as a white solid. MS: $(M+1)^+=386.1$. $^1$H NMR (DMSO-$d_6$) δ 9.15 (bm, 1H), 9.11 (s, 1H), 8.48 (bs, 1H), 8.00 (bm, 3H), 7.44 (bs, 1H), 4.69 (bm, 1H), 4.37 (bm, 1H), 3.64-3.56 (bm, 5H), 3.4-3.1 (bm, number of protons obscured by water peak and residual dioxane), 2.93 (bs, 2H), 2.58 (bm, 2H), 1.85, (s, 3H).

Example 3

Stability of Compound 45 Versus N-Acetylcysteine Amide (NACA)

The stability of Compound 45 and N-acetylcysteine amide (NACA) were determined using reversed-phase HPLC quantitation of the appearance of degradation products (impurities) after storage of the compounds for 1 or 2 months at 5° C., 25° C./60% relative humidity (RH), and 40° C./75% RH.

The chromatographic system used was an Agilent 1100 HPLC comprised of a degasser (model G1322A), pump (model G1311A), autosampler (model G1329A), column compartment (model G1316A), and a diode array detector (model G1315A). Agilent Chemstation software Rev. B.03.02 [341] was used to acquire and analyze all chromatographic data. Diluted samples and standards were placed into silanized amber vials for HPLC analysis, and the HPLC sample tray and samples were temperature controlled at 5° C. for the duration of the analysis. Assay, identity, and purity of Compound 45 and NACA, and quantitation of impurities arising over time, was accomplished by a reversed-phase isocratic method using a Phenomenex Synergi Polar-RP (250×4.6 mm, 4 mm) column at 15° C., 0.2% perchloric acid (PCA) in water and acetonitrile as mobile phase, UV detection at 210 nm, and a standard run time of 20 minutes. Standard solutions of Compound 45 and NACA were prepared in 0.2% perchloric acid to generate standard curves for quantitation of Compound 45 and NACA. Replicate samples of each analyte were collected at study initiation (baseline), after 1 month of storage under the various conditions and after 2 months of storage for quantitation of parent and impurities. Prior to analytical runs, the HPLC column was conditioned at 15° C. with Mobile Phase for 30-60 minutes or until baseline was stable. Sample diluent (blank) and one of the standard solutions were run prior to analytical runs to verify system performance (stable baseline and peak elution/retention time profile).

System Suitability

System suitability was determined as follows (per USP, section <621>):

| Parameter | Formula | Criteria |
|---|---|---|
| Retention Time | NA | NACA: 4.5-5.5 min. Compound 45: 6-8 min. |
| Precision | $S_R(\%) = \frac{100}{X}\sqrt{\frac{\sum_{i=1}^{N}(X_1 - X)^2}{N-1}}$ | % RSD(area) ≤ 2.0 (n = 6 Compound 45) |
| Column Efficiency | $N = 16\left(\frac{t}{W}\right)^2$ | N ≥ 5,000 (NACA and Compound 45) |
| Tailing Factor (Compound 45 and NACA) | $T = \frac{W_{0.05}}{2f}$ | 0.5 < T < 2.5 |
| Standard Agreement (NACA and Compound 45) | $\% \text{ Diff} = \frac{|RF_{STD-2} - RF_{STD-1}|}{RF_{STD-1}} \times 100$ | % Diff ≤ 2.0 |
| Resolution (Between NACA and Compound 45) | $R = \frac{2(t_2 - t_1)}{W_2 + W_1}$ | $R_2 \geq 1.5$ |

$S_R$ (%) Percent relative standard deviation (% RSD)
X Arithmetic mean of the peak area responses
$X_i$ Individual peak area response
N Number of injections (6)
t Retention time of the substance
W Width at base of peak measured by extrapolating the relatively straight sides to the baseline
$W_{0.05}$ The peak width at 5% peak height
f Distance from the peak maximum to the leading edge of the peak, the distance being measured at a point 5% of the peak height from the baseline
$RF_{STD-1}$ Response factor for STD-1.
$RF_{STD-2}$ Response factor for STD-2.
$t_2$ Retention time of component 2
$t_1$ Retention time of component 1
W1, W2 The corresponding widths at the bases of the peaks obtained by extrapolating the relatively straight sides of the peaks to the baseline.
Determination of standard response factor:

$RF = A_{STD}/C_{STD}$

Where:
$A_{STD}$ Peak area response for the specified standard.
$C_{STD}$ Standard concentration corrected for purity.

Analysis

Identity

The agreement of the peak for Compound 45 and NACA in the chromatograms of the sample solutions (assay and purity) and reference standard solutions was determined with respect to retention time. The difference in retention times for each did not exceed ±2.0%.

Assay

Compound 45: The peak areas of Compound 45 in the chromatograms of the sample solutions and of the Standards were determined. The amount of Compound 45 in each sample was calculated using the following equation:

$$\text{Amount (mg)} = \frac{A_u \times C_{std} \times V_s}{A_s}$$

The % Assay was determined using the following equation:

$$\% \text{ Assay} = \frac{\text{Amount}}{W} \times 100$$

Where:
$C_{std}$ Concentration (in mg/mL) of the Compound 45 STD solution
$A_u$ Peak area for Compound 45 in the Sample Preparation
$A_s$ Average peak area response for the bracketing Compound 45 STD preparations
Vs Sample dilution volume
W Weight of the sample NACA: The peak areas of NACA in the chromatograms of the sample solutions and of the standards were determined. The amount of NACA in each sample was calculated using the following equation:

$$\text{Amount (mg)} = \frac{A_u \times C_{std} \times V_s}{A_s}.$$

The % Assay was determined using the following equation:

$$\% \text{ Assay} = \frac{\text{Amount}}{W} \times 100.$$

Where:
$C_{std}$ Concentration (in mg/mL) of the Compound 45 STD solution
$A_u$ Peak area for Compound 45 in the Sample Preparation
$A_s$ Average peak area response for the bracketing Compound 45 STD preparations
$V_s$ Sample dilution volume
W Weight of the sample Purity The peak areas for all known and unknown impurities or degradation products were determined individually in the chromatograms of the sample solutions and all unknown impurities were identified by relative retention time vs. Compound 45 or NACA. All peaks relating to the solvent were disregarded. The relative retention time (RRT) of each impurity peak was calculated using the following equation:

$$RRT = \frac{RT_{imp}}{RT_{Parent}}$$

Where:
$RT_{imp}$ Retention time of the individual impurity (known or unknown)
$RT_{Parent}$ Retention time of Compound 45 or NACA (depending on sample assayed)
Impurities and degradation products were quantitated as % area vs. total using the following equation:

$$\% \text{ impurity} = \frac{A_{imp}}{A_{Total} \times RRF}.$$

Where:
$A_{imp}$ Peak area for Impurity in the Sample Preparation
$A_{Total}$ Peak area response for all non-diluent peaks in the Sample Preparation
RRF Relative Response Factor of the impurity or degradation product (if determined)
Results Both Compound 45 and NACA demonstrated temperature- and time-dependent degradation, particularly when stored at high temperature and humidity (40° C./75% RH). The extent of degradation of NACA was markedly greater than that of Compound 45 as measured by the percent change from baseline in impurities.

Figure 2:
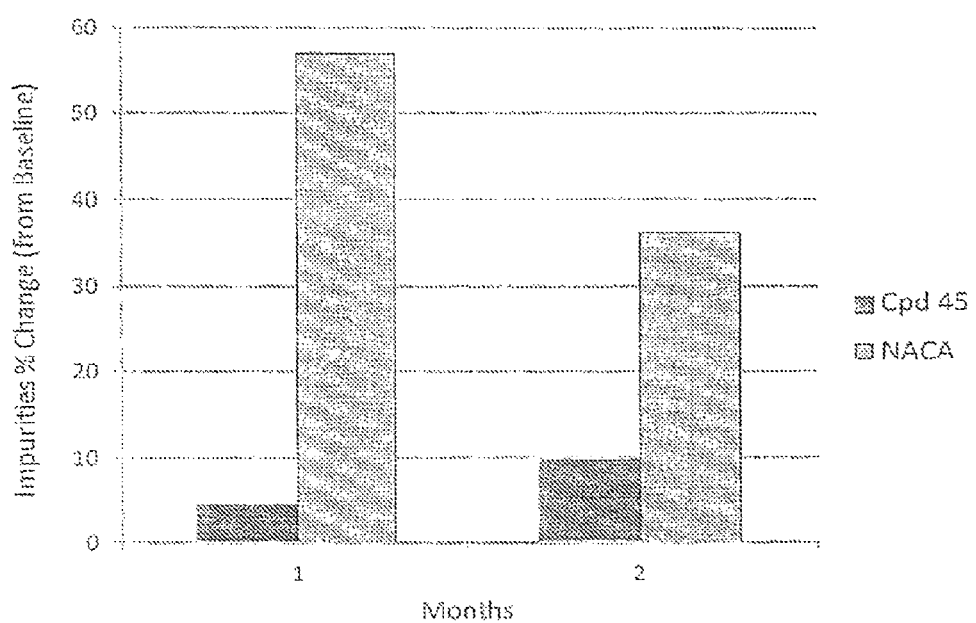
FIG. 2. Shows stability data for Compound 45 and NACA, as measured by content of impurities, after storage for one or two months at 25° C. and 60% RH.
Figure 3:
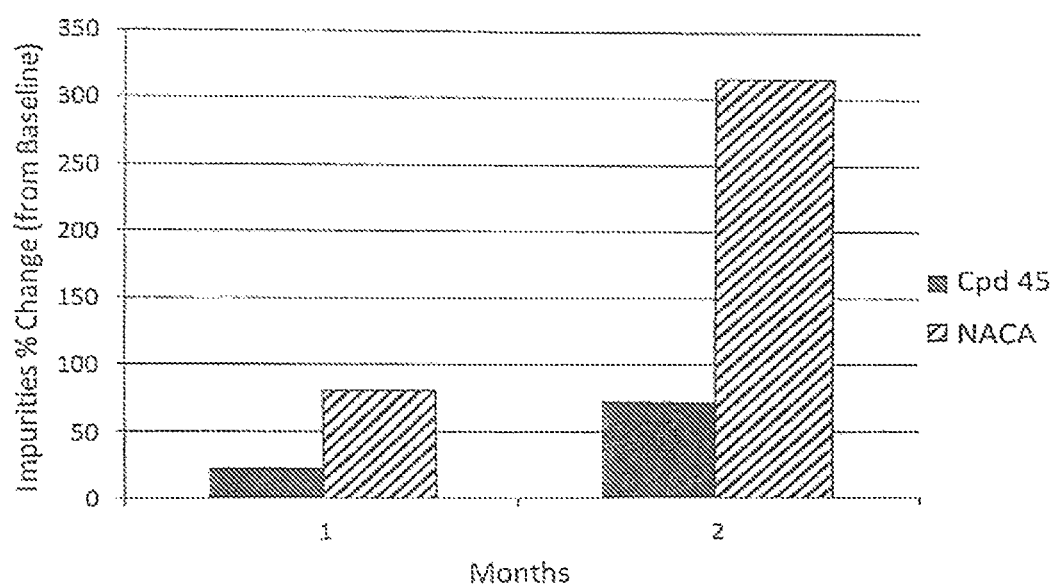
FIG. 3. Shows stability data for Compound 45 and NACA, as measured by content of impurities, after storage for one or two months at 40° C. and 75% RH.

As shown in figures, 1, 2 and 3, the percent increase in impurities from baseline for Compound 45 was less than the increase in impurities for NACA, after storage for one and two months. FIG. 1 shows the data for storage at 5° C. and 60% RH. FIG. 2 shows the data for storage at 25° C. and 60% RH. FIG. 3 shows the data for storage at 40° C. and 75% RH. These data demonstrate that Compound 45 degraded less than NACA under a broad range of storage conditions.

Example 4

Differential Solubility of Compound 45 vs Carnosine

The solubility of Compound 45 and carnosine in physiologic buffer (phosphate buffered saline, pH 7.4; PBS) were determined using a BMG Labtech NEPHELOstar nephelometer (Offenburg, Germany) with Galaxy analytical software, version 4.32R2. Stock solutions of each compound were prepared initially in dimethyl sulfoxide (DMSO); Compound 45 was soluble at a concentration of 50 mM in DMSO, while carnosine was not. Subsequently, dilution series of both compounds were prepared directly in PBS (pH 7.4) for evaluation of solubility using nephlometry, with a top concentration of 500 mg/mL for each compound and serial 1:2 dilutions. A positive control compound was included to qualitatively illustrate concentration-solubility relationships using heat maps. Compound 45 was soluble in physiologic buffer at a concentration of 500 mg/mL, while carnosine was soluble only at concentrations of ≤250 mg/mL.

Example 5

Hydrolysis of a Multifunctional Antioxidant Molecule in Whole Blood, Releasing Two Antioxidants with Different Mechanisms of Action Compound 45 is a unique multi-functional antioxidant molecule that is metabolized via enzymatic hydrolysis of the core thioester linkage to yield carnosine, an endogenous peptide antioxidant molecule, and N-acetylcysteine amide (NACA), a thiol-containing synthetic antioxidant. Carnosine has been demonstrated to scavenge free radicals and lipid peroxides, quench α,β-unsaturated aldehydes, prevent non-enzymatic glycosylation, and to prevent formation of advanced protein glycation end products. NACA is a potent thiol reducing agent, cysteine/glutathione prodrug, and free-radical scavenger. In order to validate the mechanism of metabolism of the stabilizing thioester linkage to yield the pharmacologically active, multifunctional antioxidant products, a series of experiments were performed to evaluate the hydrolysis of Compound 45 in human blood to measure the disappearance of Compound 45 and appearance of the multifunctional antioxidant components of the molecule.

To determine hydrolysis of Compound 45 and appearance of NACA and carnosine in blood, samples of human whole blood from healthy donors anti-coagulated with sodium heparin were thermally equilibrated to, and maintained at 37° C. in a water bath. Compound 45 was then spiked from a single freshly prepared stock solution into blood aliquots to create separate samples of varying Compound 45 starting concentrations (135 μM, 13.5 μM, 10.9 μM [5 μg/mL], and 2.2 μM [1 μg/mL]). Immediately after spiking, tubes were mixed by very gently rocking tubes manually for 5 minutes to ensure homogeneity and remained in the 37° C. water bath until all time points were collected. At various time points per sample concentration, tubes were removed from the bath, mixed well by gentle, manual rocking, and a 1 mL volume of Compound 45 fortified whole blood was removed from each sample, placed in a new tube, and centrifuged for 15 minutes at 5° C. to create plasma. Plasma supernatant was immediately harvested, and frozen at −80° C. until all time points were collected. Plasma samples were processed for quantitation of the disappearance (hydrolysis) of Compound 45 and the appearance of NACA or carnosine, as described below.

Sample Preparation:

Stocks Solutions: NACA, 500 μg/mL, was prepared as a solution in 1 mM ascorbic acid containing 0.05% formic acid. Compound 45, 500 μg/mL, was prepared as a solution in 15 mM perchloric acid. Carnosine, 500 μg/mL, was prepared as a solution in 15 mM perchloric acid. Maleimide reagent (N-[2-aminoethyl]maleimide), 13 mg/mL (~51 mM) was prepared as a solution in 0.1% formic acid. Sample buffer was 0.1 M ammonium acetate, pH 5.

Sample Preparation: Plasma was separated from a whole blood samples at specified time points by centrifugation at ~3000 rpm for 15 minutes. The plasma layer was separated and stored frozen (≤−20° C.) until extraction. Sample processing and extraction was accomplished in 96-well plates containing 75 μL aliquots of thawed plasma to which were added 150 μL of 1 M acetate buffer and 75 μL of 13 mg/mL Maleimide reagent to derivative NACA, generating a NACA-thio-ether product. The plates were capped and mixed well via shaking and vortexing and then centrifuged and refrigerated at 2-8'C for 5 minutes. 50 μL aliquots of derivatized samples were transferred to a new 96-well plate, and to each aliquot of derivatized sample 500 μL of acetonitrile-formic acid (100:0.1) was added. Plates were capped and shaken/vortexed to mix/extract the samples, then centrifuged to separate supernatant. 400 μL of the resulting supernatants were transferred to a new 96-well plate, and the extraction solvent was evaporated at room temperature under a gentle stream of nitrogen. Extracted samples were reconstituted in 400 μL of 0.1% formic acid in acetonitrile for analysis by HPLC-MS and the plates were sealed for injection.

Separation and Detection:

Samples in 96-well plates were analyzed on a Waters Acquity UPLC™ liquid chromatograph interfaced with a Thermo Scientific TSQ Vantage triple quadrupole mass spectrometer with electrospray ionization in the positive ion mode. Each extracted sample was injected (10 μL) onto a Waters BEH Amide column (2.1×50 mm; 1.7 μm) equilibrated at 70° C. Mobile phase A was water containing 0.2% (v/v) formic acid. Mobile Phase B was methanol containing 02% (v/v) formic acid.

HPLC separation was accomplished using the following gradient scheme:

| Time (min) | Flow Rate (mL/min) | % A | % B |
| --- | --- | --- | --- |
| 0.00 | 1.00 | 4.0 | 96.0 |
| 0.60 | 1.00 | 4.0 | 96.0 |
| 1.50 | 1.00 | 45.0 | 55.0 |
| 1.90 | 1.00 | 45.0 | 55.0 |
| 2.00 | 1.00 | 4.0 | 96.0 |

Compound 45, Carnosine and the NACA-thio-ether derivative product eluted at approximately 1.3 minutes. Compound 45 was detected by selected reaction monitoring of the mass-to-charge (m/z) 371 to 110 transition. Carnosine was detected by selected reaction monitoring of the m/z 227 to 110 transition. The NACA derivative product was detected by selected reaction monitoring of the m/z 303 to 199 transition. Raw data from the mass spectrometer was acquired and processed in Thermo Scientific Watson Laboratory Information Management System (LIMS) or in LCquan. Separate experiments were analyzed to quantitate the appearance of NACA and of carnosine from the hydrolysis of Compound 45.

Figure 4:
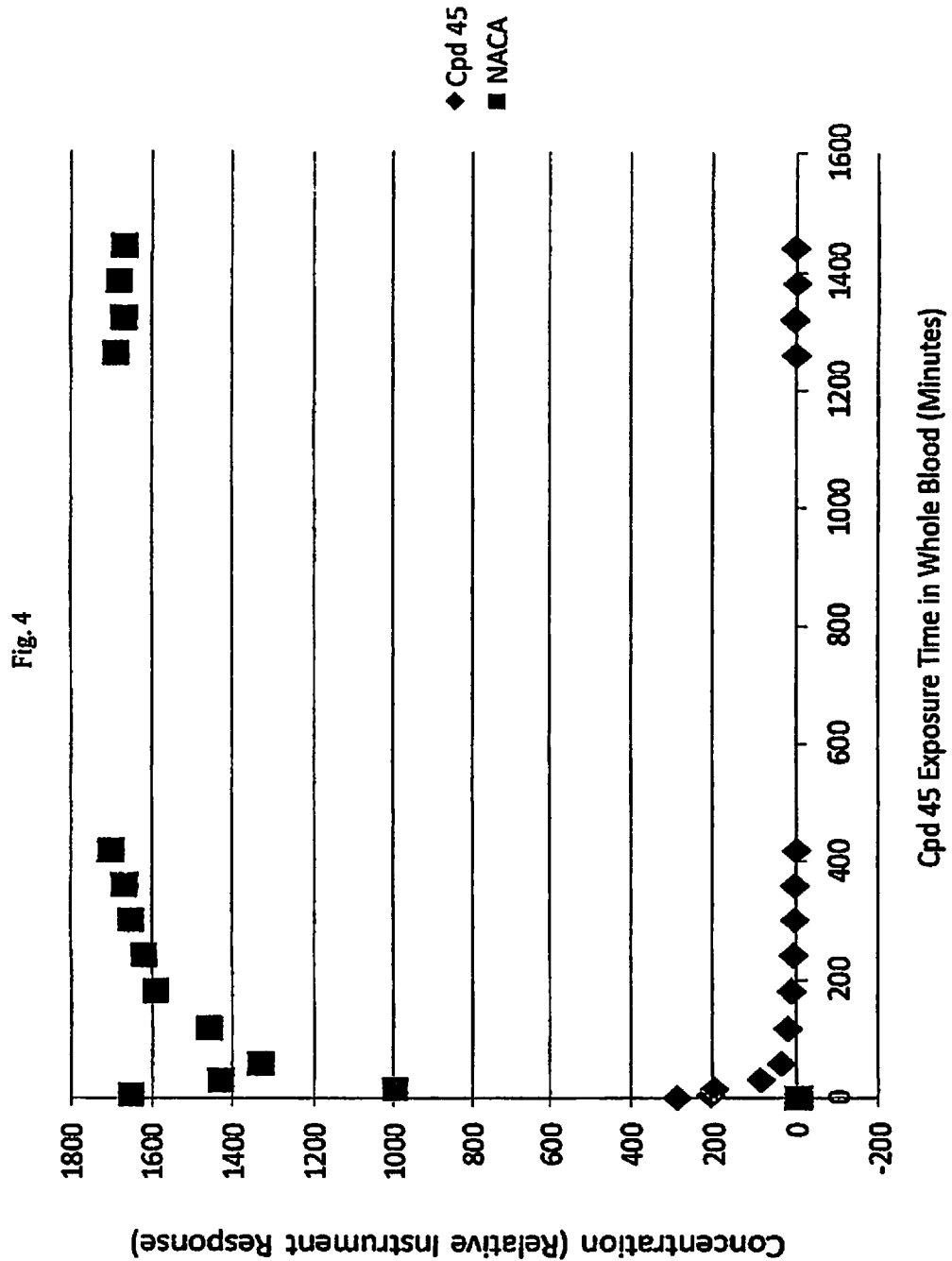
FIG. 4. Shows the hydrolysis in human whole blood of Compound 45 to yield NACA where the starting concentration of Compound 45 was 135 µM.
Figure 5:
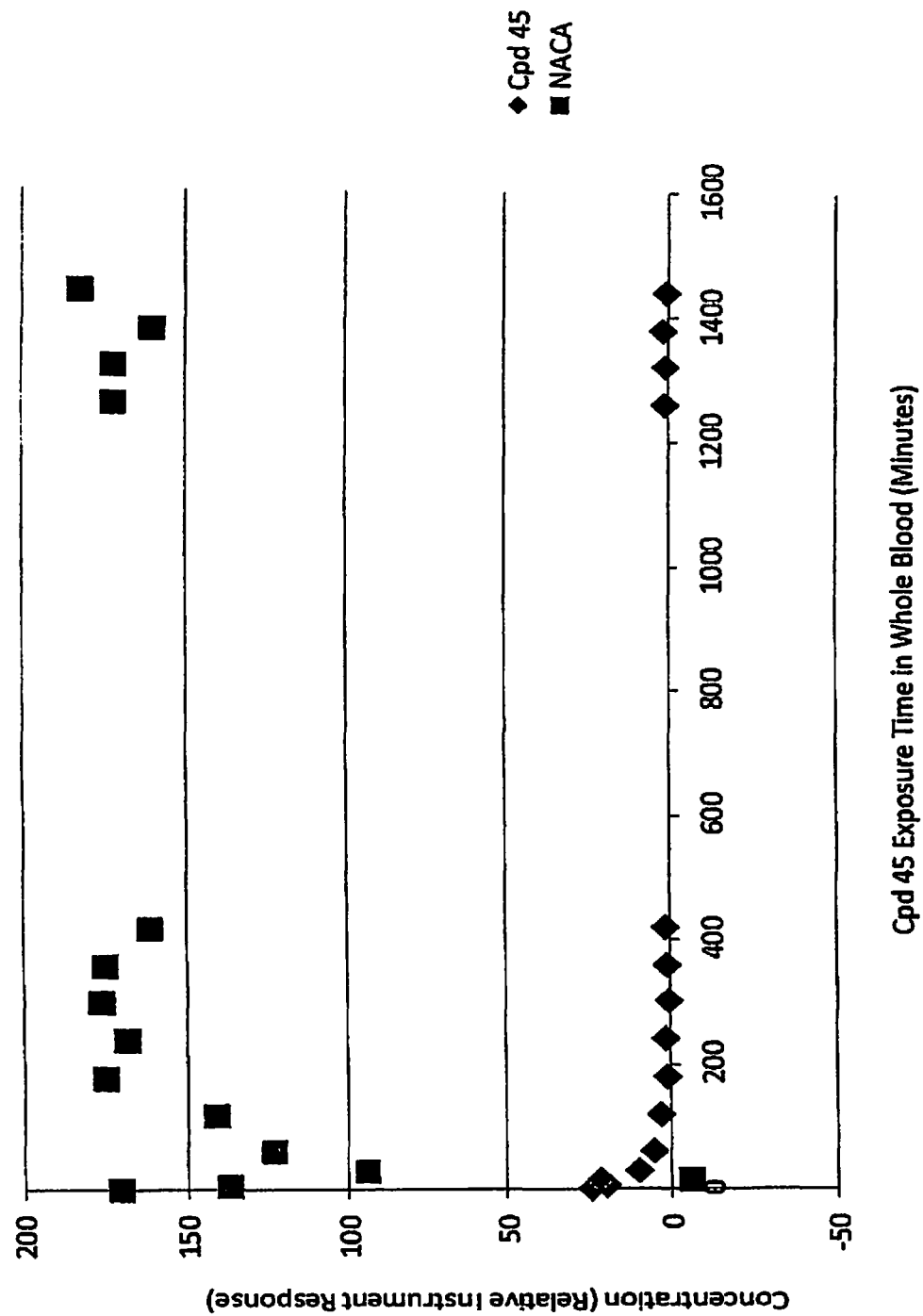
FIG. 5. Shows the hydrolysis in human whole blood of Compound 45 to yield NACA where the starting concentration of Compound 45 was 13.5 µM.
Figure 6:
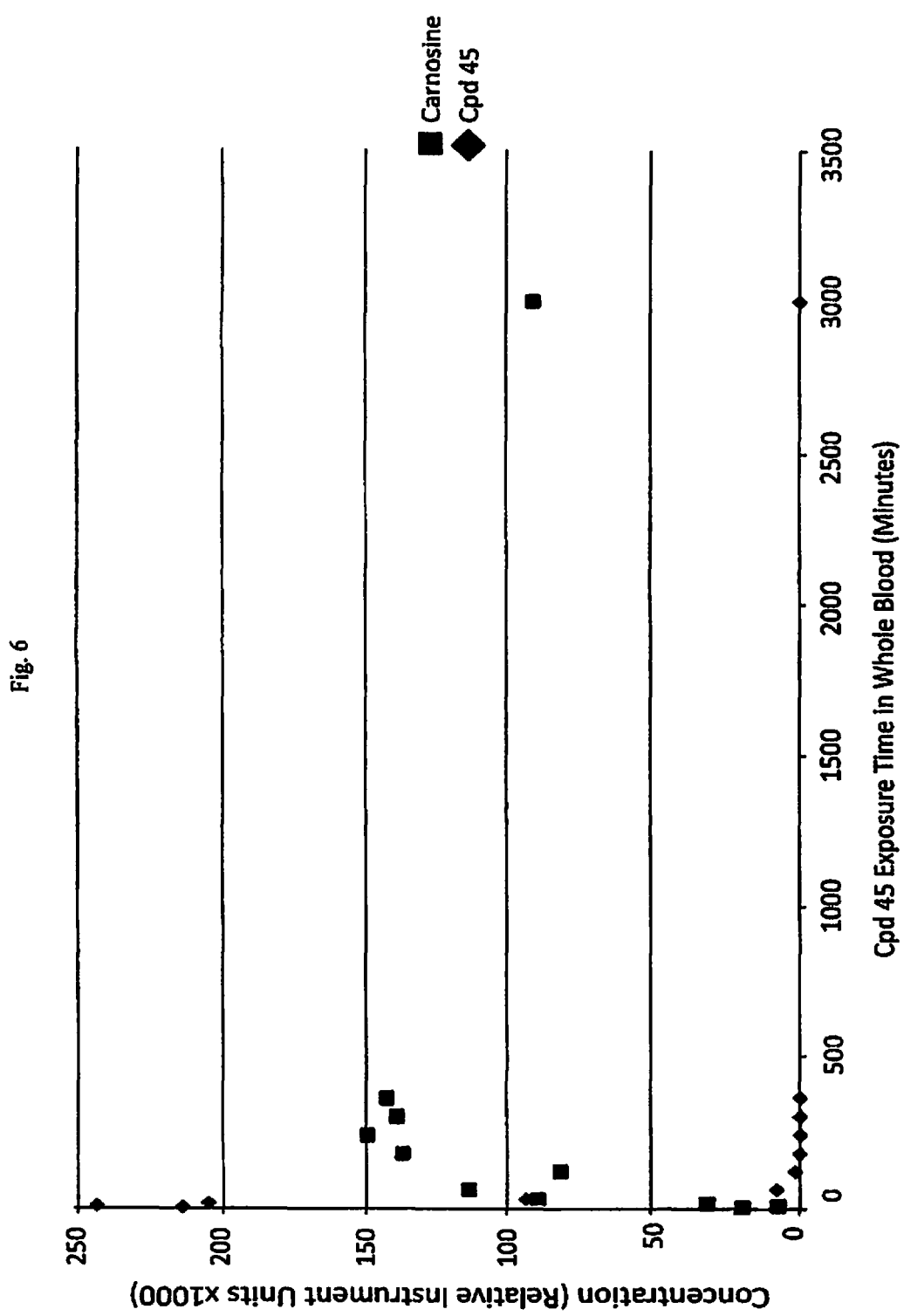
FIG. 6. Shows the hydrolysis in human whole blood of Compound 45 to yield carnosine where the starting concentration of Compound 45 was 10.9 µM (5 µg/mL).
Figure 7:
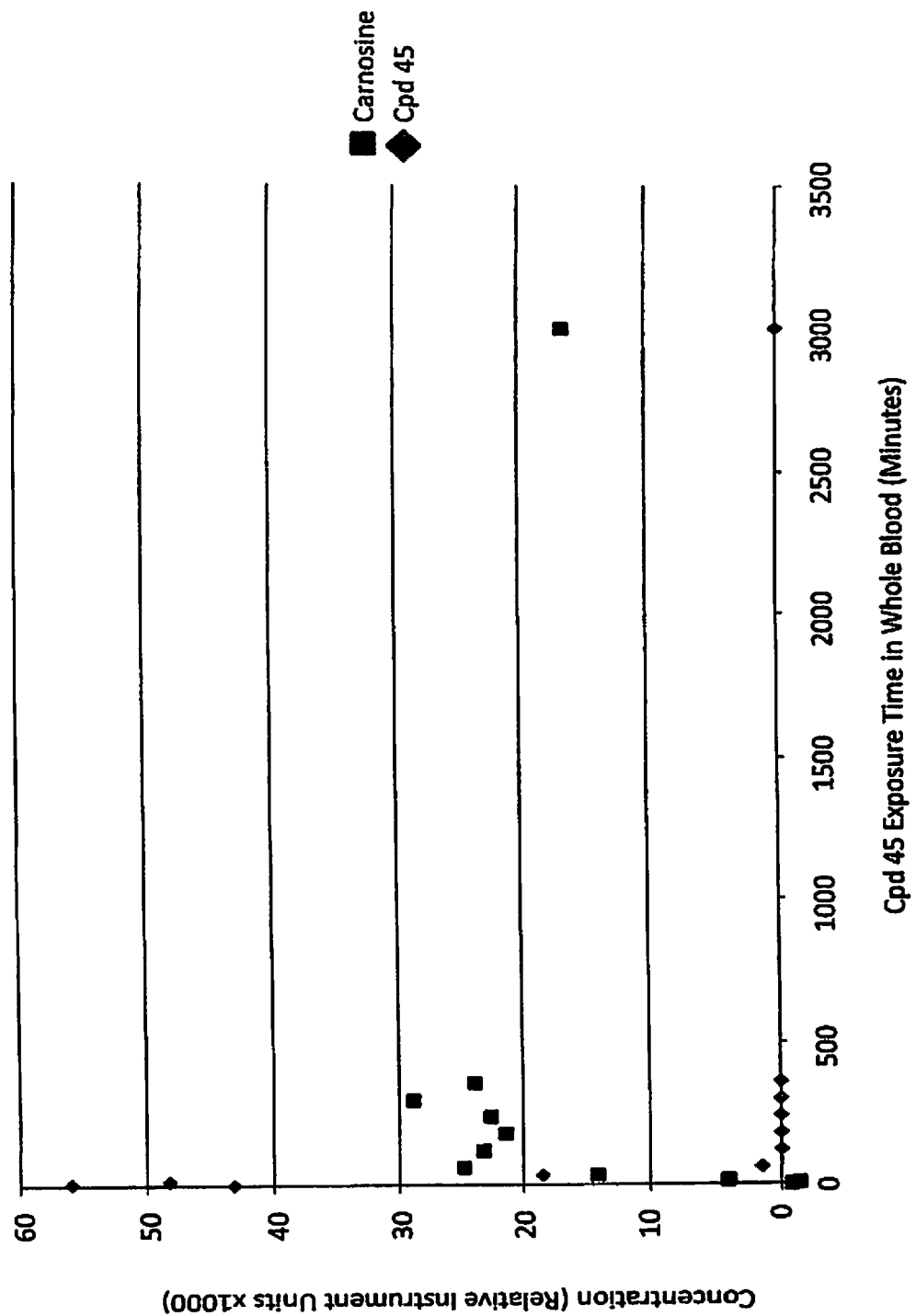
FIG. 7. Shows the hydrolysis in human whole blood of Compound 45 to yield carnosine where the starting concentration of Compound 45 was 2.2 µM (1 µg/mL).

When incubated in human whole blood, Compound 45 hydrolyzes to yield NACA (FIGS. 4 and 5) and carnosine (FIGS. 6 and 7). Thus, while the unique thioester chemical linkage stabilized the multifunctional antioxidant molecule ex-vivo, it is rapidly metabolized in blood to yield the two component multifunctional antioxidants.

Embodiments of compounds, compositions and methods are provided for illustrative purposes and are not to be considered limitations on the scope of compounds, compositions and methods of the present disclosure. The scope of this invention is to be defined by the claims rather than by the specifically described embodiments and examples.

What is claimed is:

1. A compound of Formula II:

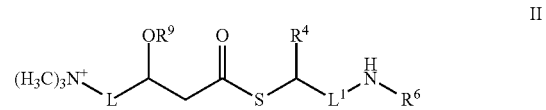

or a pharmaceutically acceptable salt thereof, wherein:
wherein
L is —$(CH_2)_m$—;
$L^1$ is —$CH(R^5)$—, or —$C(=O)$—;
$L^2$ is —O—, or —NH—;
$R^4$ is H, or $C_{1-6}$ alkyl;
$R^5$ is H, —C(O)OH, or —$C(=O)L^2 R^7$;
$R^6$ is H, or —$(CH_2)_n C(=O)R^8$;
$R^7$ is H, $C_{1-6}$ alkyl, or —$(CH_2)_p C(=O)OH$;
$R^8$ is —OH, —$CH_3$, —$CH_2 C(=O)OH$, or —$(CH_2)_w$—$CH(NH_2)$—$C(=O)OH$;
$R^9$ is H, $C_{1-6}$ alkyl, or —$C(=O)C_{1-6}$ alkyl;
m is 1, 2, 3, or 4; and
n, p, and w, are each independently 0, 1, 2, 3, or 4.

2. The compound according to claim 1, wherein
L is $CH_2$;
$R^4$ is H;
$R^6$ is —C(O)Me;
$R^9$ is H, —C(O)Me, or —C(O)Et;
$L^1$ is —$CHR^5$; and
$R^5$ is —COOH, or —$C(O)NH_2$.

3. The compound according to claim 1, wherein the compound is selected from
(2R)-4-(2-acetamido-2-carboxyethylthio)-2-hydroxy-N,N,N-trimethyl-4-oxobutan-1-aminium;
(2R)-4-(2-acetamido-3-amino-3-oxopropylthio)-2-hydroxy-N,N,N-trimethyl-4-oxobutan-1-aminium;
(2R)-4-(2-acetamido-2-carboxyethylthio)-2-acetoxy-N,N,N-trimethyl-4-oxobutan-1-aminiutn;
(2R)-4-(2-acetamido-3-amino-3-oxopropylthio)-2-acetoxy-N,N,N-trimethyl-4-oxobutan-1-aminium;
(2R)-4-(2-acetamido-2-carboxyethylthio)-N,N,N-trimethyl-4-oxo-2-(propionyloxy)butan-1-aminium; or
(2R)-4-(2-acetamido-3-amino-3-oxopropylthio)-N,N,N-trimethyl-4-oxo-2-(propionyloxy)butan-1-aminium.

4. The compound according to claim 3, wherein the compound is (2R)-4-(2-acetamido-2-carboxyethylthio)-2-hydroxy-N,N,N-trimethyl-4-oxobutan-1-aminium.

5. The compound according to claim 3, wherein the compound is (2R)-4-(2-acetamido-3-amino-3-oxopropylthio)-2-hydroxy-N,N,N-trimethyl-4-oxobutan-1-aminium.

6. The compound according to claim 3, wherein the compound is (2R)-4-(2-acetamido-2-carboxyethylthio)-2-acetoxy-N,N,N-trimethyl-4-oxobutan-1-aminium.

7. The compound according to claim 3, wherein the compound is ((2R)-4-(2-acetamido-3-amino-3-oxopropylthio)-2-acetoxy-N,N,N-trimethyl-4-oxobutan-1-aminium.

8. The compound according to claim 3, wherein the compound is (2R)-4-(2-acetamido-2-carboxyethylthio)-N,N,N-trimethyl-4-oxo-2-(propionyloxy)butan-1-aminium.

9. The compound according to claim 3, wherein the compound is (2R)-4-(2-acetamido-3-amino-3-oxopropylthio)-N,N,N-trimethyl-4-oxo-2-(propionyloxy)butan-1-aminium.

* * * * *

UNITED STATES PATENT AND TRADEMARK OFFICE
CERTIFICATE OF CORRECTION

PATENT NO. : 9,593,079 B2  
APPLICATION NO. : 15/066487  
DATED : March 14, 2017  
INVENTOR(S) : Marc Bailie et al.

Page 1 of 1

It is certified that error appears in the above-identified patent and that said Letters Patent is hereby corrected as shown below:

In the Claims

Column 44, Line 37, in Claim 3, delete "aminiutn" and replace with "aminium"

Signed and Sealed this  
Third Day of April, 2018

Andrei Iancu  
*Director of the United States Patent and Trademark Office*